(12) United States Patent
Klaiman et al.

(10) Patent No.: US 11,901,077 B2
(45) Date of Patent: Feb. 13, 2024

(54) MULTIPLE INSTANCE LEARNER FOR PROGNOSTIC TISSUE PATTERN IDENTIFICATION

(71) Applicant: HOFFMANN-LA ROCHE INC., Little Falls, NJ (US)

(72) Inventors: Eldad Klaiman, Penzberg (DE); Jacob Gildenblat, Holon (IL)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 376 days.

(21) Appl. No.: 17/376,796

(22) Filed: Jul. 15, 2021

(65) Prior Publication Data
US 2021/0350176 A1  Nov. 11, 2021

Related U.S. Application Data

(63) Continuation of application No. PCT/EP2020/056174, filed on Mar. 9, 2020.

(30) Foreign Application Priority Data

Mar. 12, 2019 (EP) ..................................... 19162244
Mar. 28, 2019 (EP) ..................................... 19165967

(51) Int. Cl.
*G16H 15/00* (2018.01)
*G16H 50/20* (2018.01)
(Continued)

(52) U.S. Cl.
CPC ........... *G16H 50/20* (2018.01); *G06F 3/0482* (2013.01); *G06F 18/214* (2023.01);
(Continued)

(58) Field of Classification Search
CPC ........ G16H 50/20; G16H 30/40; G16H 70/40; G06F 3/0482; G06F 18/214;
(Continued)

(56) References Cited

U.S. PATENT DOCUMENTS

| 10,445,879 | B1 * | 10/2019 | Fuchs ................... G06N 20/00 |
| 2009/0116737 | A1 | 5/2009 | Kiraly et al. |
| 2018/0089496 | A1 | 3/2018 | Molin et al. |

FOREIGN PATENT DOCUMENTS

| CN | 103154933 A | 6/2013 |
| CN | 108140239 A | 6/2018 |

(Continued)

OTHER PUBLICATIONS

Office Action for European Application No. 20 708 112.6 dated Jul. 13, 2023.

(Continued)

*Primary Examiner* — Neil R McLean
(74) *Attorney, Agent, or Firm* — HARNESS, DICKEY & PIERCE, P.L.C.

(57) ABSTRACT

The method includes receiving digital images of tissue samples of patients, the images having assigned a label indicating a patient-related attribute value; splitting each received image into a set of image tiles; computing a feature vector for each tile; training a Multiple-Instance-Learning program on all the tiles and respective feature vectors for computing for each of the tiles a numerical value being indicative of the predictive power of the feature vector associated with the tile in respect to the label of the tile's respective image; and outputting a report gallery including tiles sorted in accordance with their respectively computed numerical value and/or including a graphical representation of the numerical value.

20 Claims, 12 Drawing Sheets
(4 of 12 Drawing Sheet(s) Filed in Color)

(51) Int. Cl.
| | |
|---|---|
| G16H 30/40 | (2018.01) |
| G06F 3/0482 | (2013.01) |
| G06V 20/69 | (2022.01) |
| G06F 18/214 | (2023.01) |
| G06F 18/22 | (2023.01) |
| G06F 18/40 | (2023.01) |
| G06F 18/21 | (2023.01) |
| G06V 10/762 | (2022.01) |
| G06V 10/774 | (2022.01) |
| G06V 10/80 | (2022.01) |
| G06V 10/44 | (2022.01) |

(52) U.S. Cl.
CPC ........ *G06F 18/217* (2023.01); *G06F 18/2163* (2023.01); *G06F 18/22* (2023.01); *G06F 18/40* (2023.01); *G06V 10/454* (2022.01); *G06V 10/763* (2022.01); *G06V 10/774* (2022.01); *G06V 10/809* (2022.01); *G06V 20/695* (2022.01); *G06V 20/698* (2022.01); *G16H 30/40* (2018.01); *G06V 2201/03* (2022.01)

(58) Field of Classification Search
CPC .... G06F 18/2163; G06F 18/217; G06F 18/22; G06F 18/40; G06F 18/232; G06F 18/254; G06V 10/454; G06V 10/763; G06V 10/774; G06V 10/809; G06V 20/695; G06V 20/698; G06V 2201/03; G06T 2207/10024; G06T 2207/10056; G06T 2207/10064; G06T 2207/20081; G06T 2207/20084; G06T 2207/30024; G06T 7/0012; G06T 7/44; Y02A 90/10; G06N 20/00; G16B 15/30
USPC ........................................................ 382/128
See application file for complete search history.

(56) References Cited

FOREIGN PATENT DOCUMENTS

| EP | 3300001 A2 | 3/2018 |
|---|---|---|
| EP | 3300001 A3 | 5/2018 |
| WO | WO-2014089241 A2 | 6/2014 |
| WO | WO-2015073935 A1 | 5/2015 |
| WO | WO-2016061586 A1 | 4/2016 |
| WO | WO-2019/020556 A1 | 1/2019 |

OTHER PUBLICATIONS

Pooya Mobadersany et al: "Predicting cancer outcomes from histology and genomics using convolutional networks", Proceedings of the National Academy of Sciences, vol. 115, No. 13, Mar. 12, 2018 (Mar. 12, 2018), pp. E2970-E2979, XP055722606, ISSN: 0027-8424, DOI: 10.1073/pnas. 1717139115.

Gabriele Campanella et al., "Terabyte-scale Deep Multiple Instance Learning for Classification and Localization in Pathology", arxiv. org, Cornell University Library, 201 Olin Library Cornell University Ithaca, NY 14853, May 18, 2018 (May 18, 2018).

Robert W. Veltri et al., "Long-Term assessment of prostate cancer progression free survival: Evaluation of pathological parameters, nuclear shape and molecular biomarkers of pathogenesis", Prostate., vol. 68, No. 16, Dec. 2008 (Dec. 2008), p. 1806-1815,.

Maximilian Ilse et al., "Attention-based Deep Multiple Instance Learning", arxiv.org, Cornell University Library, 201 Olin Library Cornell University Ithaca, NY 14853, Jun. 28, 2018 (Jun. 28, 2018).

Daisuke Komura et al., "Luigi: Large-scale histopathological image retrieval system using deep texture representations", New York, USA DOI: 10.1101/345785 external link Jul. 19, 2018 (Jul. 19, 2018).

Talha Qaiser et al., "Her2 Challenge Contest: A Detailed Assessment of Automated Her2 Scoring Algorithms in Whole Slide Images of Breast Cancer Tissues", arxiv.org, Cornell University Library, 201 Olin Library Cornell University Ithaca, NY 14853, May 23, 2017 (May 23, 2017).

Ian Goodfellow et al., "Batch and Minibatch Algorithms", "Deep Learning", p. 271-279, Nov. 18, 2016 (Nov. 18, 2016), MIT Press, XP055621783.

International Search Report PCT/ISA/210 and Written Opinion of the International Searching Authority PCT/ISA/237 for International Application No. PCT/EP2020/056174 dated Aug. 21, 2020.

Jane Bromley et al., 'Signature Verification using a "Siamese" Time Delay Neural Network,' 1994, NIPS'1994, pp. 737-744.

Elad Hoffer et al., 'Semi-Supervised Deep Learning By Metric Embedding,' ICLR 2017, Nov. 4, 2016, <https://openreview.net/forum?id=r1 R5Z19le>.

Olaf Ronneberger et al., 'U-Net: Convolutional Networks for Biomedical Image Segmentation,' Computer Science Department and BIOSS Centre for Biological Signalling Studies, University of Freiburg, Germany, vol. 1, May 18, 2015.

Spyros Gidaris et al., 'Unsupervised Representation Learning By Predicting Image Rotations,' ICLR 2018, Feb. 15, 2018.

Boris Babenko, 'Multiple Instance Learning: Algorithms and Applications,' 2008.

Pierre Courtiol et al., 'Classification and Disease Localization In Histopathology Using Only Global Labels: A Weakly-Supervised Approach,' arXiv:1802.02212, submitted on Feb. 1, 2018, <https://arxiv.org/pdf/1802.02212.pdf>.

Mathilde Caron et al., 'Deep Clustering for Unsupervised Learning of Visual Features,' CoRR, 1807.05520, 2018.

Raia Hadsell et al., 'Dimensionality Reduction by Learning an Invariant Mapping,' CVPR 06, 2006.

International Preliminary Report on Patentability for PCT/EP2020/056174 dated Sep. 23, 2021.

Sirinukunwattana Korsuk et al: "Locality Sensitive Deep Learning for Detection and Classification of Nuclei in Routine Colon Cancer Histology Images", IEEE Transactions on Medical Imaging, IEEE Service Center, Piscataway, NJ, US, vol. 35, No. 5, May 1, 2016 (May 1, 2016), pp. 1196-1206, XP011607920, ISSN: 0278-0062, Doi: 10.1109/TMI.2016.2525803 [retrieved on Apr. 29, 2016].

Gabriele Campanella et al., "Terabyte-scale Deep Multiple Instance Learning for Classification and Localization in Pathology," Memorial Sloan Kettering Cancer Center, Sep. 2018, pp. 1-18.

Maximillian Ilse et al., "Attention-based Deep Multiple Instance Learning," Proceedings of the 35th International Conference on Machine Learning, Stockholm, Sweden, 2018, pp. 1-16.

Chinese Office Action, dated Aug. 31, 2023, issued in corresponding Chinese Patent Application No. 202080014846.4.

\* cited by examiner

Fig. 13

MULTIPLE INSTANCE LEARNER FOR PROGNOSTIC TISSUE PATTERN IDENTIFICATION

CROSS-REFERENCE TO RELATED APPLICATIONS

This application is a Continuation of PCT International Application No. PCT/EP2020/056174 which has an International filing date of Mar. 9, 2020, which claims priority to European Patent Application Nos. 19162244.8, filed Mar. 12, 2019 and 19165967.1, filed Mar. 28, 2019 the entire contents of each of which are hereby incorporated by reference.

FIELD OF THE INVENTION

The invention relates to the field of digital pathology, and more particular to the field of image analysis.

Background and Related Art

Several image analysis methods are known which can be used to aid the diagnosis process and the identification of a suitable treatment based on the analysis of tissue sample images.

Some image analysis techniques are based on using different procedures to search for structures in an image that are known to serve as indicators of the presence of a particular disease and/or the possibility of successful treatment of that disease with a particular drug. For example, some drugs used in the course of immunotherapy in cancer patients only work if certain immune cells are found at a certain distance from the cancer cells. In this case, an attempt is made to automatically recognize these objects, i.e. certain cell types or certain sub- and super-cellular structures, in a tissue image in order to be able to make a statement about the presence and/or recommended treatment of a disease. The disadvantage of this method is that the image analysis algorithms only recognize those structures for which they were developed. This type of image analysis is therefore based on existing medical knowledge about the relationships between certain cells and tissue structures and certain diseases or their treatment options. Hence, this image analysis approach is not suited for detecting unknown predictive features concerning a certain disease and/or its treatment and is limited to the medical knowledge available at a certain time. It is not suitable to extend the knowledge of medical relations, i.e. to identify hitherto unknown characteristics and tissue structures that allow a prediction to be made as to whether a certain form of the disease is present and/or whether a certain drug is effective in this disease.

Other image analysis methods, in particular non-supervised machine-learning methods, are capable of also taking into account tissue patterns and characteristics whose predictive power is unknown to the professional world and/or which are not noticeable to a pathologist in the analysis of images, since these characteristics can, for example, be derived characteristics which result from the presence, absence and/or expressiveness of several other characteristics. A disadvantage of these methods is that they usually work like a black box. In other words, a pathologist who uses these techniques must rely on the predictive power of these algorithms, without being able to specify exactly which tissue trait was ultimately decisive for the prediction. This can be a significant disadvantage, for example in the approval of drugs, because for this purpose the group of patients who benefit from a certain treatment must be specified explicitly. It is also unsatisfactory for physicians and patients alike to have to rely completely or partially on this "black box" when deciding whether the administration of a potentially effective but side-effect rich drug to a certain patient makes sense, without being able to verbalize the underlying "decision logic".

SUMMARY

It is an objective of the present invention to provide for an improved method of identifying tissue patterns being indicative of a patient-related attribute value and a corresponding image analysis system as specified in the independent claims. Embodiments of the invention are given in the dependent claims. Embodiments of the present invention can be freely combined with each other if they are not mutually exclusive.

In one aspect, the invention relates to a method of identifying tissue patterns being indicative of a patient-related attribute value. The method comprises:

receiving, by an image analysis system, for each patient in a group of patients, at least one digital image of a tissue sample of the patient, the at least one image having assigned one out of at least two different predefined labels, each label indicating a patient-related attribute value of the patient whose tissue is depicted in the labeled image;

splitting, by the image analysis system, each received image into a set of image tiles, each tile having assigned the label assigned to the image used for creating the tile;

for each of the tiles, computing, by the image analysis system, a feature vector comprising image features extracted selectively from a tissue pattern depicted in the said tile;

training a Multiple-Instance-Learning (MIL) program on all the tiles and respective feature vectors of all images received for all patients in the group, each set of tiles being treated by the MIL program as a bag of tiles having the same label, the training comprising analyzing the feature vectors for computing for each of the tiles a numerical value being indicative of the predictive power of the feature vector associated with the tile in respect to the label assigned to the image from which the tile was derived; and outputting, via a GUI of the image analysis system, an image tile report gallery, the report gallery comprising a subset of the tiles, the subset of tiles being sorted in accordance with their respectively computed numerical value and/or comprising a graphical representation of their respective numerical value.

This method may be advantageous because it may combine the advantages of image analysis methods based on explicit biomedical expert knowledge with the advantages of machine learning methods: In machine learning, multiple-instance learning (MIL) is a type of supervised learning. Instead of receiving a set of instances which are individually labeled, the learner receives a set of labeled bags, each containing many instances. In the simple case of multiple instance binary classification, a bag may be labeled negative if all the instances in it are negative. On the other hand, a bag is labeled positive if there is at least one instance in it which is positive. From a collection of labeled bags, the learner tries to either (i) induce a concept that will label individual instances correctly or (ii) learn how to label bags without inducing the concept. Convenient and simple example for MIL was given in Babenko, Boris. "Multiple instance learning: algorithms and applications" (2008). However, MIL programs according to some embodiments also cover the training based on more than two different labels (end-point).

According to embodiments of the present invention, the MIL program is used to calculate the predictive value for each instance (tile) of a bag (preferably all tiles of one or more images of tissue sections of a certain patient with a certain label value) and thus also for the tissue patterns respectively depicted in the tiles. In this step new biomedical knowledge can be identified by the MIL program, because in the training data the labels of the images and the respective tiles are given as end points for the training, but not the individual features of the feature vectors derived from the tiles which correlate strongly (positively or negatively) with the label and which are therefore predictive for this label. In addition, the predictive value calculated for the individual tiles is also output together with a graphic representation of the associated tiles in a gallery. For example, the tiles in the gallery can be sorted in accordance with the numerical value. In this case, the position of the tiles in the gallery allows a pathologist or other human user to identify the tissue pattern depicted in the ones of the tiles found to be highly predictive for a particular label. In addition, or alternatively, the numerical value can be displayed in spatial proximity to its respective tile, thereby enabling the user to inspect and comprehend the tissue pattern of the tissue depicted in one or more tiles having a similar numerical value in respect to a particular label.

Hence, the image tile gallery generated as the output of the training phase may reveal tissue signatures which are predictive in respect to a particular patient-related attribute value of a patient. Presenting the numerical value in combination with the image tiles may have the benefit that at least in many cases the predictive tissue pattern (which may also be referred to as "tissue signature") can be identified and verbalized by a pathologist by comparing several tiles in the gallery having a similar numerical value with other tiles having a much higher or much lower numerical value and by comparing the tissue signature depicted in these sub-set of tiles in the report gallery.

In a further beneficial aspect, using a MIL-program that treats image tiles as instances and the totality of all tiles of all images of the same patient having assigned a particular label (e.g. "responsive to drug D=true", "microsatellite status=MSX", "HER2 expression status=+") is particularly suited for predicting the patient-related feature in the context of whole slide tissue sample images. This is because often whole slide tissue samples cover many different tissue regions only some of which may have any predictive value. For example, a micrometastase may only be a few millimeters in diameter but the slide and the respective whole-slide image may be many cm long. Although the whole image is labeled—in accordance with the empirical observation for the patient from whom the sample was derived—with a particular label, e.g. "responsive to drug D=true", the tissue region around the micrometastase that comprises many immune cells and that is predictive for the positive response may also cover only a few millimeters. Hence, the majority of the tiles do not comprise any tissue region that is predictive in respect to the image-wise and typically patient-wise label. MIL programs are particularly suited for identifying predictive features based on bags of data instances where a large portion of the instances is assumed not to be of any predictive value.

According to embodiments the received digital images comprise digital images of tissue samples whose pixel intensity values correlate with the amount of a non-biomarker specific stain, in particular H&E stain.

For example, each bag of tiles can represent a respective patient whose responsiveness to a particular drug is known. The instances contained in this patient-specific bag are tiles derived from one or more images of respective tissue samples of this particular patient, the tissue samples having been stained with a non-biomarker specific stain such as H&E. All tissue images of this patient, and hence all the tiles derived therefrom, have assigned the label "patient responded to drug D=true".

This may be advantageous, because H&E stained tissue images represent the most common form of stained tissue images and this type of staining alone already reveals a lot of data that can be used for predicting the patient-related attribute value, e.g. the sub-type or stage of a particular tumor. Furthermore, many hospitals comprise large data bases of H&E stained tissue images derived from patients which have been treated many years in the past. Typically, the hospitals also have data in respect to whether or not a particular patient responded to a particular treatment or not and/or how fast or how severe the disease developed. Hence, a large corpus of training images is available that can be labeled with the respective outcomes (e.g. treatment by a particular drug successful yes/no, progression free survival longer than one year, progression free survival longer than two years, etc.).

According to embodiments the received digital images comprise digital images of tissue samples whose pixel intensity values correlate with the amount of a biomarker specific stain. The biomarker-specific stain is a stain adapted to selectively stain a biomarker contained in the tissue sample. For example, the biomarker can be a particular protein such as HER-2, p53, CD3, CD8 or the like. The biomarker specific stain can be a brightfield microscope or fluorescence microscope stain coupled to an antibody that selectively binds to the above-mentioned biomarker. For example, each bag of tiles can represent a respective patient whose responsiveness to a particular drug is known. The instances contained in this patient-specific bag are tiles derived from one or more images of respective tissue samples of this particular patient. The one or more tissue samples have been stained with one or more biomarker-specific stains. For example, the tiles can be derived from one, two or three tissue images all depicting adjacent tissue slides of the same patient having been stained with a HER2-specific stain. According to another example, the tiles can be derived from a first tissue image depicting a first tissue sample having been stained with a HER2-specific stain, and from a second tissue image depicting a second tissue sample having been stained with a p53 specific stain, and from a third tissue image depicting a third tissue sample having been stained with a FAP-specific stain. The first, second and third tissue sample are derived from the same patient. For example, they can be adjacent tissue sample slices. Although the three tissue images depict three different biomarkers, all tissue images are derived from the same patient, and hence all the tiles derived therefrom have assigned the label "patient responded to drug D=true".

Training the MIL program on image tiles of digital images whose pixel intensity values correlate with the amount of a biomarker specific stain may have the advantage that identifying the presence and position of one or more specific biomarkers in the tissue may reveal highly specific and prognostic information in respect to particular diseases and sub-forms of diseases. The prognostic information may comprise observed positive and negative correlations of the presence of two or more of the biomarkers. For example, the recommended treatment scheme and prognosis of some diseases such as lung cancer or colon cancer have been observed to strongly depend on the mutational signature and expression profile of the cancer. Sometimes, the expression of a single marker alone does not have predictive power, but a combined expression of multiple biomarkers and/or the absence of a particular further biomarker may have high predictive power in respect to a particular patient-related attribute value.

According to embodiments the received digital images comprise a combination of digital images of tissue samples whose pixel intensity values correlate with the amount of a first biomarker specific stain and of digital images of tissue samples whose pixel intensity values correlate with the amount of a non-biomarker specific stain. A biomarker-specific stain is a stain adapted to selectively stain a biomarker contained in the tissue sample. All digital images depicting the same tissue sample and/or depicting adjacent tissue samples from the same patient have assigned the same label. The MIL is configured to treat all tiles derived from said digital images as members of the same bag of tiles.

This approach may have the advantage that identifying the presence and position of one or more specific biomarkers in the tissue in combination with the information-rich tissue signatures revealed by H&E staining may provide highly specific and prognostic information in respect to particular diseases and sub-forms of diseases. The prognostic information may comprise observed positive and negative correlations of the presence of two or more of the biomarkers and/or of tissue signatures visually revealed by a H&E staining.

According to embodiments, the image tiles shown in the image tile report gallery are derived from one or more different ones of the received images. The method comprises, for each of the one or more images depicted in the report tile gallery:

Identifying the one of the tiles in the report gallery having been derived from the said image and having assigned the highest score of all the tiles derived from said image; according to one embodiment, this score is the numerical value computed for each tile by the MIL; according to an alternative embodiment, this score is a weight computed for each tile by an attention-MLL as described herein for embodiments of the invention; according a still further embodiment, this score is a combination of the said numerical value computed by the MIL and the said weight computed by the attention MLL for said tile, whereby the combination can be, for example, a multiplication of the numerical value and the weight;

For each of the other tiles of the image, computing a relevance indicator by comparing the score of the other tile with the score of the tile having the highest score; the relevance indicator is a numerical value that negatively correlates with the difference of the score of the other tile with the score of the tile having the highest score;

Computing a relevance heat map for the image as a function of the relevance indicator; thereby, the pixel color and/or pixel intensities of the relevance heat map are indicative of the relevance indicator computed for the tiles in the said image; and displaying the relevance heat map. For example, the relevance heat map can be displayed in the report tile gallery in spatial proximity to the whole slide image for which the relevance heat map was computed.

For example, image regions and respective tiles that have a score that is highly similar to the score of the highest-scoring tile of an image can be represented in the relevance heat map with a first color (e.g. "red") or a high intensity value and image regions and respective tiles whose score is dissimilar to the highest score of a tile of this image can be represented in the relevance heat map with a second color that is different from the first color (e.g. "blue") or a low intensity value.

This may be advantageous, because the GUI automatically computes and presents a relevance heat map that indicates the position and coverage of the tissue regions and respective image tiles having a high predictive power (or "prognostic value"). The relevance heat map may highlight tissue regions having a high relevance indicator. A tile is typically only a small subregion of the whole-slide image and the report tile gallery as such may not provide an overview over the whole tissue sample. The overview information regarding the position and coverage of tissue patterns with high predictive relevance may be provided by the relevance heat map that is preferably combined with the original image of the whole slide tissue image in a highly intuitive and smart manner.

Computing the relevance heat map based on the numerical values of the MIL may have the advantage that it may not be necessary to implement and train an attention-MLL. Hence, the system architecture may be easier to implement.

Computing the relevance heat map based on the weights computed by an attention-MLL may have the advantage that a second numerical measure for the prognostic relevance of a tile in addition to the numerical value of the MIL is evaluated and represented in the relevance heat map.

Computing the relevance heat map based on a combined relevance score derived from the numerical value computed by the MIL and from the weight computed by the attention MLL for a particular tile may have the advantage that two independently computed numerical measures for the prognostic relevance of a tile are integrated in and represented by the combined value and by the relevance heat map that is based on the combined values. This may increase the accuracy of the identification of relevant tissue sections.

According to embodiments, the GUI enables the user to select whether the relevance heat map is computed based on the numerical values of the MIL or based on the weights of the attention-MLL or based on the combined score. This may allow a user to identify if the output of the MIL and of the attention MLL in respect to the predictive power of a tile is significantly different.

Computing and displaying the relevance heat map may be advantageous as this heat map is indicative of the predictive power of tiles in respect to the endpoint used for training the MIL and/or the attention-MLL. Hence, displaying the relevance heat map to a user enables the user to quickly identify the position and coverage of tiles having a tissue pattern that is predictive for a particular label within a whole slide image.

According to embodiments, the image tiles shown in the report gallery are selectable. The GUI is configured for computing and displaying a similarity search tile gallery, the computation comprising:

Receiving a user's selection of a particular one of the report gallery image tiles;

Identifying all tiles obtained from all the received images that depict a similar tissue pattern as the selected tile by identifying all tiles obtained from all the received images that have assigned a feature vector whose similarity to the feature vector of the selected tile exceeds a threshold value; and Displaying a similarity search gallery, the similarity search gallery selectively comprising the said identified tiles.

According to embodiments, the computing and displaying of the similarity search tile gallery further comprises:

Determining the number and/or fraction of tiles within said tiles that depict a similar tissue pattern as the selected tile which have assigned the same label as the selected tile; and Displaying the determined number and/or fraction in the similarity search gallery.

These features may be advantageous, because a human user is enabled to quickly determine how common a particular tissue pattern is among the patient group examined and in the sub-set of the patients having a particular label. Hence, the human user is enabled to quickly and intuitively verify whether a particular tile and the tissue pattern depicted therein really has high predictive power.

For example, the user may select the one of the tiles of the report gallery having assigned the highest numerical value and hence the highest predictive power in respect to a label of the image. After having selected the tile, the user may initiate a tile-based similarity search across the tiles and images of many different patients which may have assigned a different label than the currently selected tile. the similarity search is based on a comparison of the feature vectors and the tiles for determining similar tiles and similar tissue patterns based on similar feature vectors. By evaluating and displaying the number and/or fraction of tiles (and respective tissue patterns) which are similar to the selected tile (and its tissue pattern) but have a different label than the label of the selected tile (e.g. "patient responded to drug D=false" rather than "patient responded to drug D=true").

Hence, the pathologist can easily check the predictive power, in particular sensitivity and specificity, of the tissue pattern identified by the MIL program by selecting a tile that is returned by the MIL program as "highly prognostic" for performing a similarity search that reveals how many of the tiles in the data set which have a similar feature vector have assigned the same label as the selected tile. This is a great advantage over state-of-the-art machine learning applications which may also provide an indication of prognostic features of a tissue image but we do not allow a user to identify and verify those features. Based on the report gallery and the similarity search gallery, a human user can verify the proposed highly prognostic tissue patterns and can also verbalize common features and structures that are shown in all tiles having high predictive power and that are associated with similar feature vectors.

The feature that the tiles in the report gallery are selectable and a selection triggers the performing of a similarity search for identifying and displaying other tiles having a similar feature vector/tissue pattern as the user-selected tile may enable a user to freely select any image tile in the report tile gallery he or she is interested in. For example, the pathologist can be interested in the tissue pattern and respective tiles having the highest predictive power (the highest numerical value computed by the MIL) as mentioned above. Alternatively, the pathologist can be interested in artifacts which typically have a particular low predictive power (a particular low numerical value). Still alternatively, the pathologist can be interested in a particular tissue pattern for any other reason, e.g. because it reveals some side effect of a drug or any other biomedical information of relevance. The pathologist is free to select any one of the tiles in the respective report tile gallery. Thereby, the pathologist triggers the similarity search and the computation and display of the results in the form of a similarity tile gallery. The display and the GUI can be refreshed automatically after the similarity search has completed.

According to some embodiments, the computation and display of the similarity search gallery comprises the computation and display of a similarity heat map. The heat map encodes similar tiles and respective feature vectors in colors and/or in pixel intensities. Image regions and tiles having similar feature vectors are represented in the heat map with similar colors and/or high or low pixel intensities. Hence, a user can quickly get an overview of the distribution of particular tissue pattern signatures in a whole slide image. The heat map can easily be refreshed simply by selecting a different tile, because the selection automatically induces a re-computation of the feature vector similarities based on the feature vector of the newly selected tile.

According to embodiments, the similarity search gallery comprises a similarity heat map. The method comprises creating the similarity heat map by a sub-method comprising:

Selecting one of the tiles in the report tile gallery;

For each of the other tiles of some or all of the received images, computing a similarity score in respect to the selected tile by comparing the feature vector of the other tiles derived from the same and from other images with the feature vector of the selected tile;

Computing, for each of the images whose tiles were used for computing a respective similarity score, a respective similarity heat map as a function of the similarity scores, the pixel color and/or pixel intensities of the similarity heat map being indicative of the similarity of the tiles in the said image to the selected tile; and displaying the similarity heat map.

According to embodiments, also the image tiles shown in the similarity search gallery are selectable.

The similarity heat maps may provide valuable overview information that allows a human user to easily perceive how widespread a particular tissue pattern of interest occurs in a particular tissue or in the tissue samples of a sub-group of patients having a particular label. A user can freely select any of the tiles in the search gallery, thereby respectively inducing a re-computation of the similarity heat map based on the feature vector assigned to the currently selected tile, and an automatic refresh of the GUI comprising the similarity heat map.

According to embodiments, the image tiles in the report gallery and/or in the similarity search tile gallery are grouped based on the patients from whose tissue sample images the tiles were derived. According to alternative embodiments, the image tiles in the report gallery and/or in the similarity search tile gallery are grouped based on the label assigned to the image from which the tiles were derived.

Typically, all images derived from the same patients will have the same label and all tiles derived from those images of a particular patient will be treated by the MIL as members of the same "bag". However, in some exceptional cases, it may be that different images of the same patient have assigned different labels. For example, if the first image depicts a first metastase of a patient and a second image depicts a second metastase of the same patient and the observation is that the first metastase disappeared in response to the treatment with drug D while the second metastase continued to grow, the patient-related attribute value can be assigned image-wise instead of patient wise. In this case, there may be multiple bags of tiles per patient.

According to another example, images of tissue samples of a patient are taken before and after treatment with a particular drug and the end-point (label) used for training the MIL and/or for applying a trained MIL is the attribute value "state of tissue=after treatment with drug D" or the attribute value "state of tissue=before treatment with drug D". Training a MIL on the said patient-related attribute value may have the advantage of identifying tissue patterns which are indicative of the activity and morphological effects of the drug on the tumor. Such identified drug-effect related tissue patterns could allow verifying and exploring the drug's mode of action as well as potentially drug adverse effects.

According to embodiments, the method further comprises: Computationally increasing the number of bags of tiles by creating additional sets of tiles, each additional set of tiles being treated by the MIL program as an additional bag of tiles having assigned the same label as the tissue image from which the source tiles were generated. The creation of additional sets of tiles in particular comprises: applying one or more artifact generation algorithms on at least a subset of the tiles for creating new tiles comprising the artifact. In addition, or alternatively, the creation of additional bags of tiles can comprise increasing or decreasing the resolution of at least a sub-set of the tiles for creating new tiles being more fine-grained or more coarse-grained than their respective source tiles.

For example, a sub-set can be obtained for each of the patients by randomly selecting some or all tiles of the one or more tissue images obtained from said patient. The artifact generation algorithm simulates image artifacts. The image artifacts can be, for example, of the type of artifacts generated during tissue preparation, staining and/or image acquisition (e.g. edge artifacts, overstaining, understaining, dust, speckle artifact, (simulated by Gaussian blur, etc.). In addition, or alternatively, the artifact can be of a generic noise type (simulated e.g. by occlusion, color jittering, Gaussian noise, salt & pepper, rotations, flips, skew distortions etc.).

The creation of additional bags of tiles may have the advantage that additional training data is generated from a limited set of available training data. The additional training data represents image data whose quality may be reduced by common distortions, artifacts and noise that often occur in the context of sample preparation and image acquisition. Hence, the enlarged training data set may ensure that overfitting of the model underlying the MIL program during training is avoided.

According to embodiments, the method further comprises computing clusters of tiles obtained from the one or more received digital images, wherein tiles are grouped into clusters based on the similarity of their feature vectors. Preferably, the clusters are computed for each of the patients. This means that tiles from different images depicting different tissue slides of the same patient may be grouped into the same cluster if the feature vectors of the tiles are sufficiently similar.

According to other embodiments, the clusters are computed for all the tiles from all the patients together.

In both methods for clustering (all tiles of different patients together or per patient) tiles that look similar to each other (i.e., have similar feature vectors) are clustered into the same cluster.

For example, in case of the "all tiles of different patients clustering", a result of the clustering could be the generation of e.g. 64 groups (clusters) of tiles for all tiles for all the patients. Each of the 64 clusters comprises similar tiles derived from different patients. To the contrary, in the case of a per patient clustering, each patient would have his own 64 clusters.

If clusters are created per patient, it could be that a patient image has no tiles containing fat or very few tiles containing fat. In this case a "fat cluster" might not be created since there is not enough data for learning a cluster around that "fat"-characteristic feature vector. But performing a clustering method on all the tiles of all patients together may have the advantage that a larger number of clusters/tissue types may be identified with the maximum amount of data available: In a "all-patient-tile" clustering, a cluster for the "fat" tissue pattern will likely be identified, because at least some patients will have some fat cells in their biopsy. Hence, the probability that the number of fat cell depicting tiles in the data set is sufficient, a cluster for fat cell would be created (also for the patients with very little fat cell content) If clusters are created for all tiles of all patients together and one cluster represents fat cells, all tiles with fat cells from all of the patients would be grouped in that cluster. This means that for a specific patient/bag all tiles with fat cells would be grouped together in the said cluster and if cluster sampling is used for that bag, some amount of tiles (from the current patient/bag) that belong to said cluster will be selected.

The clustering of tiles may be advantageous as this operation may reveal the number and/or type of tissue patterns observable in a particular patient. According to some embodiments, the GUI comprises a user-selectable element that enables a user to trigger the clustering of tiles and the presentation of the tile clusters in a clustered gallery view. This may assist a user in intuitively and quickly understanding important types of tissue patterns observed in a particular tissue sample of a patient.

According to embodiments, the training of the MIL program comprises repeatedly sampling the sets of tiles for picking sub-sets of tiles from the sets of tiles, and training the MIL program on the sub-sets of tiles.

The term "sampling" as used herein is a technique used in the context of data analysis or of training a machine learning algorithm that comprises picking a specifically chosen number of L samples (here: instances, i.e., tiles) out of a number of N data items (instances, tiles) in a dataset (the totality of tiles obtained from one or more images of a patient). According to embodiments, the 'sampling' comprises selecting a subset of data items from within the number of N data items in accordance with a probability distribution assumed to statistically represent the totality of N tiles in the trainings data set. This may allow learning the characteristics of the whole population more accurately. The probability distribution represents a statistical assumption that guides the machine learning process and makes 'learning from data' feasible.

According to some embodiments, the sampling is performed by randomly selecting subsets of tiles for providing sampled bags of tiles.

According to embodiments, the clustering and the sampling are combined as follows: the sampling comprises selecting tiles from each of the tile clusters obtained for a patient such that the number of tiles in each sub-set of tiles created in the sampling corresponds to the size of the cluster from which the said tile is taken.

For example, 1000 tiles may be created from a digital tissue image of a particular patient. The clustering creates a first cluster showing background tissue slide regions that comprises 300 tiles, a second cluster showing stroma tissue regions that comprises 400 tiles, a third cluster showing metastatic tumor tissue comprising 200 tiles, a fourth cluster showing a particular staining artifact comprising 40 tiles and a fifth cluster showing tissue with microvessels comprising 60 tiles.

According to one embodiment, the sampling comprises selecting from each of the clusters a particular fraction of tiles, e.g. 50%. This would mean 150 tiles from cluster 1, 200 tiles from cluster 2, 100 tiles from cluster 3, 20 tiles from cluster 4 and 30 tiles from cluster 5.

According to preferred embodiments, the sampling comprises selecting an equal number of tiles from each cluster. This sampling approach may have the advantage that the same number of tiles/tissue pattern examples from different types of clusters is drawn, thereby making the training data set more balanced. This may increase the accuracy of the trained MIL and/or of the trained attention-MLL in case the desired predictive feature is rare in the training data set.

The combination of clustering and sampling may be particularly advantageous, because the data basis for training can be increased by the sampling without unintentionally "loosing" the few tiles actually being of high predictive power. Often in the context of digital pathology, the vast majority of the area of a tissue sample does not comprise tissue regions that are modified by and that are prognostic for a particular disease or other patient-related attribute. For example, only a small sub-region of a tissue sample may actually comprise tumor cells, the rest may show normal tissue. By performing a clustering of the tiles first and then selecting tiles from each of the clusters may ensure that at least some of the few tiles showing prognostic tissue patterns, e.g. tumor cells or microvessels, are ensured to be always part of the sample.

Feature Extraction Approaches

According to embodiments, the computing of the feature vector for each of the tiles comprises receiving patient-related data of the patient whose tissue sample is depicted in the tile and representing the patient-related data in the form of one or more features in the feature vector, the patient related data being in particular selected from a group comprising genomic data, RNA sequence data, known diseases of the patient, age, sex, metabolite concentrations in a body fluid, health parameters and current medication.

According to embodiments, the computing of the feature vectors is performed by a trained machine learning logic, in particular by a trained fully convolutional neural network comprising at least one bottleneck-layer.

According to embodiments, the trained machine learning logic to be used for feature extraction ("feature extraction MLL") is trained in a supervised method by taking an MLL of type fully convolutional network that includes a bottleneck, like UNET. The "Unet" architecture is described by Olaf Ronneberger, Philipp Fischer, and Thomas Brox in "U-Net: Convolutional Networks for Biomedical Image Segmentation", Computer Science Department and BIOSS Centre for Biological Signalling Studies, University of Freiburg, Germany (arXiv:1505.04597v118 May 2015). The document can be downloaded via the Cornell University Library https://arxiv.org/abs/1505.04597.

For example, the feature extraction MLL can be trained to perform a tissue image segmentation task, whereby the segments to be identified comprise two or more of the following tissue image segment types: tumor tissue, healthy tissue, necrotic tissue, tissue comprising particular objects such as tumor cells, blood vessels, stroma, lymphocytes, etc., and background area. According to some embodiments, the feature extraction MLL is trained in a supervised manner using a classification network such as Resnet, ImageNet, or SegNet, by training it to classify tiles of images with specific predetermined classes or objects.

After the feature extraction MLL has been trained, the MLL is split into an "encoder" part (comprising the input layer, one or more intermediate layers and a bottleneck layer) and a "decoder", i.e., an output-generation part. The "encoder" part up to the bottleneck layer of the trained MLL is used according to embodiments of the invention to extract and compute the feature vector for each input tile. The bottleneck layer is a layer of a neural network that comprises significantly less neurons than the input layer. For example, the bottleneck layer can be a layer comprising less than 60% or even less than 20% of the "neurons" of the input layer. The number and ratio of the neurons in the different layers may vary a lot depending on different network architectures. The bottleneck layer is a hidden layer.

According to one example, the network of the feature-extraction MLL has a UNET based network architecture. It has an input layer of with 512*512*3 (512×512 RGB) neurons and bottleneck layer with 9*9*128 neurons. Hence, the number of neurons in the bottleneck layer is about 1.5% of the number of neurons of the input layer.

According to one example, the network of the feature-extraction MLL has a Resnet architecture that implements supervised or unsupervised learning algorithms. The input layer comprises 512×512×3 neurons and the bottleneck layer and the corresponding feature vector output by the bottleneck layer comprises typically 1024 or 2048 elements (neurons/numbers).

According to embodiments, the feature extraction is performed by a feature extraction program module that is based on the ResNet-50 (He et al., 2016) architecture trained on the ImageNet natural image dataset. Some detailed examples for feature extraction from images that is based on this architecture is described in Pierre Courtiol, EricW. Tramel, Marc Sanselme, & Gilles Wainrib: "CLASSIFICATION AND DISEASE LOCALIZATION IN HISTOPATHOLOGY USING ONLY GLOBAL LABELS: A WEAKLY-SUPERVISED APPROACH", arXiv:1802.02212, submitted on 1 Feb. 2018, available online via the Cornell University Library https://arxiv.org/pdf/1802.02212.pdf.

According to embodiments, the output generated by one of the layers of the trained feature extraction MLL for a particular tile is used as the feature vector extracted from the tile by the MIL program. This one layer can be, in particular, the bottleneck layer. According to embodiments, the feature extraction MLL is trained in an unsupervised or self-supervised manner as described in Mathilde Caron and Piotr Bojanowski and Armand Joulin and Matthijs Douze: "Deep Clustering for Unsupervised Learning of Visual Features", CoRR, 1807.05520, 2018 that is electronically available via https://arxiv.org/abs/1807.05520.

Alternatively, the feature extraction MLL can be trained in accordance with Spyros Gidaris, Praveer Singh, Nikos Komodakis: "Unsupervised Representation Learning by Predicting Image Rotations", 15 Feb. 2018, ICLR 2018 Conference electronically available via https://openreview.net/forum?id=S1v4N2I0-.

Still alternatively, the feature extraction MLL can be trained in accordance with Elad Hoffer, Nir Ailon. "Semi-supervised deep learning by metric embedding", 4 Nov. 2016, ICLR 2017 electronically available via https://openreview.net/forum?id=r1R5Z19Ie.

The dataset for training the feature extraction MLL can be another tissue image dataset and/or the set of tissue images that is later used for training the MIL program. Any labels associated with the training images are not evaluated or otherwise used by the feature extraction MLL in the training phase as the feature extraction MLL is trained for identifying tissue types and respective image segments rather than the patient-related attribute value of the patient that is used as the end-point of the learning phase of the MIL program.

Feature Extraction Approaches Making Use of Proximity-Based Similarity Labels

According to embodiments, the feature vectors are computed by a feature extraction machine learning logic ("feature extraction MLL") having been trained on a training data set comprising labeled tile pairs, whereby each label represents the similarity of two tissue patterns depicted by the tile pair and is computed as a function of the spatial distance of two tiles of the tile pair.

According to preferred embodiments, each label represents the similarity of two tissue patterns depicted by the tile pair and is computed as a function of the spatial distance of two tiles of the tile pair, thereby using the spatial distance as the only measure of similarity of the two tiles.

According to preferred embodiments, the labels are assigned to the tile pairs in the training data set fully automatically.

This approach may be beneficial for multiple reasons: spatial proximity of two image regions is a feature that is always and inherently available in every digital image of a tissue sample. The problem is that spatial proximity of image and respective tissue regions per se typically do not reveal any relevant information in respect to a biomedical problem such as tissue type classification, disease classification, the prediction of the durability of a particular disease or an image segmentation task. Applicant has surprisingly observed that the information conveyed in the spatial proximity of two image regions ("tiles") is an accurate indicator of the similarity of the two image regions, at least if a large number of tiles and their respective distances is analyzed during the training phase of an MLL. Hence, by making use of the inherently available information "spatial proximity" of two tiles for automatically assigning a tissue pattern similarity label to the two compared tiles, a large annotated data set can be provided automatically that can be used for training a MLL. The trained MLL can be used for automatically determining if two images or image tiles received as input depict a similar or dissimilar tissue pattern. However, the data set can in addition be used for other and more complex tasks such as image similarity search, image segmentation, tissue type detection and tissue pattern clustering. Hence, applicant has surprisingly observed that the information conveyed in the spatial proximity of tiles can be used for automatically creating annotated training data that allows training an MLL that reliably determines the similarity of images and in addition may allow training an MLL that outputs a feature vector that can be used by additional data processing units for a plurality of complex image analysis tasks in digital pathology. None of these approaches requires a domain expert to annotate training data manually.

When a training image comprising many different tissue patterns (e.g. "non-tumor" and "tumor") is split into many different tiles, the smaller the distance between two tiles, the higher the probability that both compared tiles depict the same tissue pattern, e.g. "non-tumor". There will, however, be some tile pairs next to the border of two different patterns that depict different tissue pattern (e.g. the first tile "tumor", the other tile "non-tumor"). These tile pairs generate noise, because they depict different tissue patterns although they lie in close spatial proximity to each other. Applicant has surprisingly observed that this noise that is created by tile pairs spanning the border between different tissue patterns in combination with the simplifying assumption that spatial proximity indicates similarity of depicted tissue patterns does not reduce the accuracy of the trained MLL significantly. In fact, applicant observed that the accuracy of an MLL that was trained according to embodiments of the invention are able to outperform existing benchmark methods.

In a further beneficial aspect, it is now possible to quickly and fully automatically create training data for many different sets of images. Currently, there is a lack of available annotated datasets that capture the natural and practical variability in histopathology images. For example, even existing large datasets like Camelyon consist of only one type of staining (Hematoxylin and Eosin) and one type of cancer (Breast Cancer). Histopathology image texture and object shapes may vary highly in images from different cancer types, different tissue staining types and different tissue types. Additionally, histopathology images contain many different texture and object types with different domain specific meanings (e.g. stroma, tumor infiltrating lymphocytes, blood vessels, fat, healthy tissue, necrosis, etc.). Hence, embodiments of the invention may allow automatically creating an annotated data set for each of a plurality of different cancer types, cancer-sub-types, staining methods and patient groups (e.g. treated/non-treated, male/female, older/younger than a threshold age, biomarkerpositive/biomarker-negative, etc.). Hence, embodiments of the invention may allow automatically creating annotated training data and training a respective MLL on the training data such that the resulting trained MLL is adapted to accurately address biomedical problems for each of a plurality of different groups of patients in a highly specific manner. Contrary to state of the art approaches where a MLL trained on a manually annotated breast cancer data set provided suboptimal results for colon cancer patients, embodiments of the invention may allow creating a MLL for each of the different patient groups separately.

According to embodiments, the label being indicative of the degree of similarity of two tissue patterns is a binary data value, i.e., a value that may have one out of two possible options. For example, the label can be "1" or "similar" and indicate that the two tiles depict a similar tissue pattern. Alternatively, the label can be "0" or "dissimilar" and indicate that the two tiles depict dissimilar tissue patterns. According to other embodiments, the label can be more fine grained, e.g. can be a data value selected from a limited set of three or more data values, e.g. "dissimilar", "similar" and "highly similar". According to still other embodiments, the label can be even more fine grained and can be a numerical value, wherein the amount of the numerical value positively correlates with the degree of similarity. For example, the numerical value can be computed as a function that linearly and inversely transforms the spatial distance between the two tiles in the pair into the numerical value representing tissue pattern similarity. The larger the spatial distance, the smaller the numerical value indicating tissue pattern similarity. A large variety of MLL architectures exist which can process and use different types of labels in the training data set (e.g. ordinal or numerical values). The type of MLL is chosen such that it is able to process the automatically created labels of the training data set.

According to embodiments, the MLL that is trained on the automatically annotated training data set and that is to be used for feature extraction is adapted to learn according to a supervised learning algorithm. Supervised learning is about finding a mapping that transforms a set of input features into one or more output data values. The output data values are provided during the training as labels, e.g. as a binary option label "similar" or "non-similar" or as a numerical value that is a quantitative measure for similarity. In other words, during the training, the data values that shall be predicted are explicitly provided to the model of the MLL in the form of the labels of the training data. Supervised learning comes with the problem that the training data needs to be labeled in order to define the output space for each sample.

According to embodiments, at least some or all of the tile pairs respectively depict two tissue regions contained in the same tissue slice. Each of the tissue slices is depicted in a respective one of the received digital images. The distance between tiles is computed within a 2D coordinate system defined by the x- and y-dimension of the received digital image from which the tiles in the pair have been derived.

According to embodiments, the tile pairs are generated by randomly selecting tile pairs within each of the plurality of different images. The random based selection ensures that the spatial distance between the tiles in each pair will vary. A similarity label, e.g. in the form of a numerical value that correlates inversely with the distance between the two tiles, is computed and assigned to each pair.

According to other embodiments, the tile pairs are generated by selecting at least some or all of the tiles of each received image as a starting tile; for each starting tile, selecting all or a predefined number of "nearby tiles", wherein a "nearby tile" is a tile within a first circle centered around the starting tile, whereby the radius of this circle is identical to a first spatial proximity threshold; for each starting tile, selecting all or a predefined number of "distant tiles", wherein a "distant tile" is a tile outside of a second circle centered around the starting tile, whereby the radius of the said circle is identical to a second spatial proximity threshold; the selection of the predefined number can be performed by randomly choosing this number of tiles within the respective image area. The first and second proximity threshold may be identical, but preferably, the second proximity threshold is larger than the first proximity threshold. For example, the first proximity threshold can be 1 mm and the second proximity threshold can be 10 mm. Then, a first set of tile pairs is selected, whereby each tile pair comprises the start tile and a nearby tile located within the first circle. Each tile pair in the first set is assigned the label "similar" tissue patterns. In addition, a second set of tile pairs is selected, whereby each pair in the said set comprises the start tile and one of the "distant tiles". Each tile pair in the second set is assigned the label "dissimilar" tissue patterns. For example, this embodiment may be used for creating "binary" labels "similar" or "dissimilar".

According to embodiments, the distance between tiles is measured within the 2D coordinate system defined by the x and y axes of the digital image from which the tiles are derived. These embodiments may be used in a situation where a plurality of tissue sample images are available which depict tissue samples of different patients and/or of different regions within the same patient, whereby said different regions lie far away from each other or whereby the exact position of the said two regions relative to each other is unknown. In this case, the spatial proximity between tiles is measured only within the 2D plane of pixels defined by the digital image. Based on a known resolution factor of the image acquisition device (e.g. a camera of a microscope or a slide scanner), the distance between tiles of the original image can be used for computing the distance between the tissue regions in the tissue sample depicted by the two tiles.

According to embodiments, at least some or all of the tile pairs depict two tissue regions contained in two different tissue slices of a stack of adjacent tissue slices. Each of the tissue slices are depicted in a respective one of the received digital images. The received images depicting tissue slices of a stack of adjacent tissue slices are aligned with each other in a 3D coordinate system. The distance between tiles is computed within the 3D coordinate system.

For example some or all received digital images may depict tissue samples which are slices within a tissue block of adjacent tissue slices. In this case, the digital images can be aligned with each other in a common 3D coordinate system such that the position of the digital image in the 3D coordinate system reproduces the position of the respectively depicted tissue slices within the tissue block. This may allow determining the tile distance in a 3D coordinate system. The selection of "nearby" and "distant" tiles can be performed as described above for the 2D coordinate system case, with the only difference that the tiles in at least some of the tile pairs are derived from different ones of the received images.

According to some embodiments, the annotated training data comprises both tile pairs derived from the same digital image as well as tile pairs derived from different images having been aligned with each other in a common 3D coordinate system. This may be beneficial as the consideration of the third dimension (spatial proximity of tiles representing tissue regions in different tissue samples) may tremendously increase the number of tiles in the training data in case only a small number of images of respective tissue samples is available whereby the tissue samples belong to the same cell block, e.g. a 3D biopsy cell block.

According to embodiments, each tile depicts a tissue or background region having a maximum edge length of less than 0.5 mm, preferably less than 0.3 mm.

A small tile size may have the advantage that the number and area fraction of tiles depicting a mixture of different tissue patterns is reduced. This may help reducing the noise generated by tiles depicting two or more different tissue patterns and by tile pairs next to a "tissue pattern border" depicting two different tissue patterns. In addition, a small tile size may allow generating and labeling a larger number of tile pairs, thereby increasing the amount of labeled training data.

According to embodiments, the automatic generation of the tile pairs comprises: generating a first set of tile pairs using a first spatial proximity threshold; the two tissue regions depicted by the two tiles of each tile pair in the first set are separated from each other by a distance smaller than the first spatial proximity threshold; generating a second set of tile pairs using a second spatial proximity threshold; the two tissue regions depicted by the two tiles of each tile pair in the second set are separated from each other by a distance larger than the second spatial proximity threshold. For example, this can be implemented by selecting a plurality of start tiles, computing a first and a second circle based on the first and second spatial proximity threshold around each start tile and selecting tile pairs comprising the start tile and a "nearby tile" (first set) or a "distant tile (second set) as described already above for embodiments of the invention.

According to embodiments, the first and second spatial proximity thresholds are identical, e.g. 1 mm.

According to preferred embodiments, the second spatial proximity threshold is at least 2 mm larger than the first spatial proximity threshold. This may be advantageous, because in case the tissue pattern changes gradually from one into another pattern, the difference between the tissue pattern depicted in a "distant tile" compared to the tissue pattern depicted in a "nearby" tile may be clearer and the learning effect may be improved.

According to embodiments, the first spatial proximity threshold is a distance smaller than 2 mm, preferably smaller than 1.5 mm, in particular 1.0 mm.

In addition, or alternatively, the second spatial proximity threshold is a distance larger than 4 mm, preferably larger than 8 mm, in particular 10.0 mm.

These distance thresholds refer to the distance of the tissue regions (or slice background regions) depicted in the digital images and respective tiles. Based on a known magnification of the image acquisition device and the resolution of the digital image, this distance can be transformed in a distance within the 2D or 3D coordinate system of a digital image.

For example, the distance between tiles (and the tissue regions depicted therein) can be measured e.g. between the centers of two tiles in a 2d or 3D coordinate system. According to an alternative implementation variant, the distance is measured between the two tile edges (image region edges) lying closest to each other in the 2D or 3D coordinate system.

The above-mentioned thresholds have been observed to provide labeled training data that allows automatically generating a trained MLL that is accurately capable of identifying similar and dissimilar tissue patterns for breast cancer patients. In some other implementation examples, the first and second spatial proximity threshold may have other values. In particular in case a different set of received digital images showing different tissue types or cancer types is used, the first and second spatial proximity threshold may have other values than the above provided distance threshold values.

According to embodiments, the method further comprises creating the training data set for training the feature-extraction-MLL. The method comprises receiving a plurality of digital training images each depicting a tissue sample; splitting each of the received training images into a plurality of tiles ("feature extraction training tiles"); automatically generating tile pairs, each tile pair having assigned a label being indicative of the degree of similarity of two tissue patterns depicted in the two tiles of the pair, wherein the degree of similarity is computed as a function of the spatial proximity of the two tiles in the pair, wherein the distance positively correlates with dissimilarity; training a machine learning logic—MLL—using the labeled tile pairs as training data to generate a trained MLL, the trained MLL having learned to extract a feature vector from a digital tissue image that represent the image in a way that images that are similar have similar feature vectors and images that are dissimilar have dissimilar feature vectors; and using the said trained MLL or a component thereof as a feature extraction MLL that is used for computing the feature vectors of the tiles.

This approach may be beneficial because as the labels of the training data set can be created automatically based on information that is inherently contained in every digital pathology image, it is possible to create an annotated data set for training a feature extraction MLL that is specifically adapted to the currently addressed biomedical problem simply by choosing the training images accordingly. All further steps like the splitting, labeling and machine learning steps can be performed fully automatically or semi-automatically.

According to embodiments, the trained MLL is a Siamese network comprising two neuronal sub-networks joined by their output layer. One of the sub-networks of the trained Siamese network is stored separately on a storage medium and is used as the component of the trained MLL that is used for computing the feature vectors of the tiles.

Label Processed by the MIL Program

According to embodiments, the label is selected from a group comprising: An indication that the patient responded to a particular drug; An indication that the patient has developed metastases or a particular form of metastases (e.g. micro-metastases); An indication that a cancer patient shows a pathological complete response (pCR) in response to a particular therapy; An indication that the patient has a cancer with a particular morphological state or microsatellite status; an indication that a patient has developed adverse reaction to a particular drug; Genetic attributes, in particular gene signatures; and/or RNA expression profiles.

These labels may be helpful in diagnosis as well as in finding a suitable drug for treating a disease. However, the above-mentioned labels are only examples. Other patient-related attributes can also be used as labels (i.e., endpoints for training the MIL program) as described above. The term "patient-related" can also comprise treatment-related, because also the effectiveness of a particular treatment of a disease relates to the patient being treated.

Combination of the MIL Program and an Attention MLL

According to embodiments of the invention, the MIL program is combined with an attention based MLL for computing numerical values being indicative of the predictive power of a particular tile in respect to the label assigned to the image the tile is derived from. For example, the combination can be performed when training the MIL program as described for an embodiment of the method and a corresponding system depicted in FIG. 6. According to another example, the combination can be performed when training the MIL program as described for an embodiment of the method and a corresponding system depicted in FIG. 7.

According to embodiments, an attention MLL is a machine learning logic adapted to compute a weight indicative of the predictive power of the feature vector of a tile in respect to a label assigned to the image a tile is derived from, and the weight can then be provided as input to the MIL or can be combined with the numerical values output by the MIL.

According to embodiments, both the MIL program and the attention MLL program learn to identify feature vectors and respective tiles (and hence, the tissue pattern depicted therein) having predictive power in respect to a patient-related attribute value. The attention MLL program can be implemented as a part, e.g. a sub-module, of the MIL program.

According to some embodiments, the attention MLL program implements a permutation invariant transform operation which is used by the MIL program for aggregating the predictive power in respect to the bag's label encoded in all the feature vectors of the tiles of one bag. This permutation invariant transform generates a single, aggregate numerical value for a bag based on all the tiles. According to embodiments, the difference of the aggregated numerical value from the label actually assigned to the bag is also considered as a form of "loss" of the MIL program that is to be minimized during backpropagation. The permutation invariant transform operation is used by the MIL in the training phase but is also used by the trained MIL program at test phase.

The permutation invariant transform operation may allow specifying how the information encoded in all the tiles of a bag are taken into account during the training phase.

According to embodiments, the permutation invariant transform operation is a maximum operation. This may be beneficial as the predictive model generated when training the MIL strongly reflects the tissue pattern depicted in the tile having the feature vector with the highest predictive power in respect to the bag's label. The model is not negatively affected by tissue regions/tiles which are irrelevant for the label. However, the maximum operation will neglect all the information contained in all tiles except the highest scoring tile. Hence, the predictive power of tiles/tissue patterns which may also be of relevance may be missed.

According to embodiments, the permutation invariant transform operation is an average operation, e.g. an arithmetic mean or median of numerical values representing the predictive power of each individual feature vector in respect to a particular label. This may be beneficial as the predictive model generated when training the MIL takes into account the tissue patterns depicted in all tiles. However, the consideration of tissue patterns and respective tiles which are actually irrelevant for the occurrence of a particular label may result in a deterioration and reduction of the predictive accuracy of the trained MIL.

According to embodiments, the permutation invariant transform operation of the MIL program is an AVERAGE or MEDIAN operation.

According to one embodiment, the permutation invariant transform operation is an average operation, e.g. an arithmetic mean or median of numerical values representing the predictive power of each individual feature vector in respect to a particular label, and an attention MLL is used for computing a weight for each of the tiles. The weight computed for a particular tile and the respective feature vector represents the "attention" the MIL will draw for this tile during the training phase.

The combination of an "average" permutation invariant transform operation in combination with an attention MLL configured to compute tile-specific weights may have the advantage that the benefits provided by the AVERAGE operation (the information conveyed in all tiles are considered) can be used without accepting also the downsides of this operation (the impact of irrelevant tissue patterns on the training of the predictive model of the MIL program). This may allow improving the accuracy of the predictive model of the trained MIL program: the non-significant tiles are balanced out in the learning process by learning selectively/predominantly from tiles having assigned a higher weight.

Combining an attention MLL program and a MIL program as described herein for embodiments of the invention may have the advantage that the attention MLL program (in particular when implementing the permutation invariant transform operation other than a MAX operation, e.g. an AVERAGE or MEDIAN operation) allows the MIL program to learn from more than one instance (tile) per iteration, in contrast to e.g. a MAX operation for example which is a sparse method which selects only one instance of all the bag to learn from in each iteration. Typically, the use of an AVERAGE or MEDIAN operation is not preferable as this operation may cause a deterioration of the model learned by the MIL program caused by the feature vectors of tiles having no predictive power. However, if the feature vectors of those tiles have assigned a low weight based on an independent estimation of the attention MLL, the training process of the MIL program may benefit from using an AVERAGE or MEDIAN rather than a MAXIMUM operation as the permutation invariant transform.

For example, the use of an attention MLL when training a MIL program can be performed as described in Maximilian Ilse, Jakub M. Tomczak, Max Welling: "Attention-based Deep Multiple Instance Learning", February 2018 that is electronically available via https://arxiv.org/abs/1802.04712.

According to embodiments, the GUI is configured to create and present a heat map for the weights computed by the attention-MLL program for all tiles derived from a particular digital image. The weights are normalized, e.g. to a range from 0-1, and then the normalized weights of the tiles are color-coded. The more similar the weights of the tiles, the more similar the colors of the attention-MLL-based heat map.

Attention-MLL Program Providing Weighted Numerical Values

According to embodiments (see e.g. FIG. 6), the method comprises computing, for each of the tiles, the numerical value being indicative of the predictive power of the feature vector associated with the tile in the form of a weighted numerical value. Each weighted numerical value of a tile is computed as a function of the weight computed by the attention MLL for said tile and of the numerical value computed by the MIL for said tile. In particular, the weighted numerical values can be computed by multiplying the weight computed by the attention MLL for a tile with the numerical value of the respective tile.

Attention-MLL Program Providing Weighted Feature Vectors

According to embodiments, the method comprises computing, for each of the tiles, the feature vector in the form of a weighted feature vector. The weighted feature vector is computed as a function of the weight computed by the attention MLL for said tile and of the feature vector computed for said tile by the feature extraction program. In particular, the weights provided by the attention MLL for a particular tile can be multiplied with the feature vector of this tile.

According to another embodiment, the training of the MIL is implemented such that the numerical value output by the MIL for a particular tile in respect to a particular label and that is indicative of the predictive power of the tiles in respect to the bag's (image's) label is multiplied by the weight computed by the attention MLL for this tile. During backpropagation, the weights have an impact on the adaptation of the predictive model of the MIL. The impact of a particular feature vector on the predictive model of the MIL learned during the training positively correlates with the weight computed for a particular tile by the attention MLL.

According to one embodiment, the training of the MIL is implemented such that the weights provide by the attention MLL are provided together with the feature vectors as input of the MIL program. The training of the MIL is implemented such that the MIL learns more from tiles whose feature vector have a higher weight than from tiles whose feature vector have a lower weight. In other words, the impact of the tiles and their feature vectors on the predictive model of the MIL learned during the training positively correlates with the weight computed for a particular tile by the attention MLL.

Using an attention-MLL for computing weights for each feature vector may be advantageous as the MIL will learn more from the few tiles having high predictive potential and will learn less from the majority of tiles showing irrelevant tissue sections. As a consequence, the accuracy of the trained MIL program is increased.

FURTHER EMBODIMENTS

According to embodiments, the method further comprises:
- receiving, by the image analysis system, for each patient in a further group of patients, at least one further digital image of a tissue sample of the patient, each further image having assigned one of the predefined labels;
- splitting, by the image analysis system, each received further image into a set of further image tiles, each tile having assigned the label assigned to the image used for creating the further tile;
- for each of the further tiles, computing, by the image analysis system, a further feature vector comprising image features extracted selectively from the said further tile and from a tissue pattern depicted therein;
- applying the trained Multiple-Instance-Learning (MIL) program on the further tiles and respective further feature vectors of all further images received for all patients in the further group for computing for each of the further tiles a numerical value being indicative of the probability that the image from which the further tile was derived has assigned a particular label, the numerical value being computed as a learned non-linear transformation function of the feature vector of said further tile; and
- outputting, via the GUI of the image analysis system, a further image tile report gallery, the further report gallery comprising a plurality of the further tiles, the tiles being sorted in accordance with their respectively computed numerical value and/or comprising a graphical representation of their respective numerical value.

This may be advantageous because the trained MIL program can be applied easily on new image data, thereby easing the analysis and interpretation of the new images in respect to the patient-related attribute of interest, e.g. by automatically presenting a report gallery selectively presenting the ones of the tiles of the new images which have been identified by the trained MIL program as having high predictive power in respect to this patient-related attribute.

According to embodiments, the MIL program learns in the training phase to translate feature vectors to a value that can represent probability for a particular label. The label can represent a class (e.g. patients responding to the treatment with a particular drug D) or a numerical endpoint value (e.g. a number or percentage value indicating the degree of response). This learning can be mathematically described as the learning of a non-linear transform function that transforms the feature values into one of the labels provided during training. According to some embodiments, at testing time some minor structural changes are applied to the trained MIL program (such as disabling Dropout layers, etc.) and no sampling of the test data takes place. The main change when applying the trained MIL program at test time is that all instances (tiles) in the bags of the test data are analyzed by the MIL program to compute the final numerical values indicating the predictive power for each of the tiles and for each of a plurality of labels provided in the training phase. Finally, a final numerical value is computed for the whole image or for a particular patient by aggregating the numerical values computed for the tiles of the image for the plurality of labels. The final result of applying the trained MIL program on the one or more images of the patient is the one of the labels having the highest probability (e.g. "patient will respond to a treatment with drug D!"). In addition, the one of the tiles having the highest predictive power in respect to this label may be presented in a report image tile gallery that is structurally equivalent to the report image tile gallery described above for the training phase.

According to embodiments, the method further comprises automatically selecting or enabling a user to select one or more "high-predictive-power-tiles". A high-predictive-power-tile is a tile whose numerical value indicating the predictive power of its feature vector in respect to a particular one of the labels exceeds a high-predictive-power-threshold; and/or In addition, or alternatively, the method further comprises automatically selecting or enabling a user to select one or more "artifact-tiles". An artifact-tile is a tile whose numerical value indicates the predictive power of its feature vector in respect to a particular one of the labels is below a minimum-predictive-power-threshold or depicts one or more artifacts.

In response to the selection of one or more high-predictive-power-tiles and/or artifact-tiles, automatically re-training the MIL program, thereby excluding the high-predictive-power-tiles and artifact-tiles from the training set.

These features may have the advantage that the re-trained MIL program may be more accurate, because the excluded artifact-tiles will not be considered any more during re-training. Hence, any bias in the learned transformation that was caused by tiles in the training data set depicting artifacts is avoided and removed by re-training the MIL program on a reduced version of the training data set that does not comprise the artifact-tiles.

Enabling a user to remove highly prognostic tiles from the training data set may be counter-intuitive but nevertheless provides important benefits: sometimes, the predictive power of some tissue patterns in respect to some labels is self-evident.

For example, a tissue section comprising many tumor cells expressing a lung-cancer-specific biomarker is of course an important prognostic marker for the presence of the disease lung cancer. However, the pathologist may be more interested in some less obvious tissue patterns, e.g. the presence and/or location of non-tumor cells, e.g. FAP+ cells.

According to another example, the MIL is trained for identifying tissue patterns induced by smoking in lung cancers which may have predictive potential in respect to the label "patient shows low response to treatment with a particular drug D". The MIL may compute the highest numerical value/predictive power for a first tissue pattern corresponding to lung tissue comprising smoking-induced residues. Removal of tiles showing tissue regions with the smoking induced residues might uncover another tissue pattern having a medium-degree predictive power. In case the feature vector comprises genetical and/or physiological attribute values of a patient, the impact of the predictive power of those additional features may also become more relevant after the tiles with the highest numerical values have been "blacklisted". These genetically-related or physiologically related predictive features may also be reflected in a particular tissue pattern and hence may allow a pathologist to identify and understand the genetically-related or physiologically related attribute by inspecting the corresponding tiles in the result tile gallery generated after a re-training of the MIL on a training tile set that does not comprise the blacklisted tiles.

Hence, when all tiles showing tumor cells as the most important prognostic factors are removed and the MIL program is retrained on the remaining training dataset, the re-trained MIL will be able to identify less prominent but still significant prognostic factors and tissue patterns more reliably.

In a further aspect, the invention relates to an image analysis system for identifying tissue patterns being indicative of a patient-related attribute value. The image analysis system comprises:

at least one processor;

a volatile or non-volatile storage medium comprising digital tissue images of tissues of a group of patients, wherein for each patient in the group of patients, at least one digital image of a tissue sample of the patient is stored in the storage medium, the at least one image having assigned one out of at least two different predefined labels, each label indicating a patient-related attribute value of the patient whose tissue is depicted in the labeled image;

an image splitting module being executable by the at least one processor and being configured to split each of the images into a set of image tiles, each tile having assigned the label assigned to the image used for creating the tile;

a feature extraction module being executable by the at least one processor and being configured to compute, for each of the tiles, a feature vector comprising image features extracted selectively from a tissue pattern depicted in the said tile;

a Multiple-Instance-Learning (MIL) program being executable by the at least one processor and being configured to receive, in a training phase of the MIL program, all the tiles and respective feature vectors of all images of all patients in the group, the MIL program being configured to treat each set of tiles as a bag of tiles having the same label during the training phase, the training comprising analyzing the feature vectors for computing for each of the tiles a numerical value being indicative of the predictive power of the feature vector associated with the tile in respect to the label assigned to the image from which the tile was derived;

a GUI generation module being executable by the at least one processor and being configured to generate and output a GUI comprising an image tile report gallery, the report gallery comprising a subset of the tiles, the subset of tiles being sorted in accordance with their respectively computed numerical value and/or comprising a graphical representation of their respective numerical value; and a display adapted for displaying the GUI with the image tile report gallery.

A "tissue sample" as used herein is a 3D assembly of cells that may be analyzed by the methods of the present invention. The 3D assembly can be a slice of an assembly of an ex-vivo cell block. For example, the sample may be prepared from tissues collected from patients, e.g. a liver, lung, kidney or colon tissue sample from a cancer patient. The samples may be whole-tissue or TMA sections on microscope slides. Methods for preparing slide mounted tissue samples are well known in the art and suitable for use in the present invention.

Tissue samples may be stained using any reagent or biomarker label, such as dyes or stains, histochemicals, or immunohistochemicals that directly react with specific biomarkers or with various types of cells or cellular compartments. Not all stains/reagents are compatible. Therefore, the type of stains employed and their sequence of application should be well considered, but can be readily determined by one of skill in the art. Such histochemicals may be chromophores detectable by transmittance microscopy or fluorophores detectable by fluorescence microscopy. In general, cell containing samples may be incubated with a solution comprising at least one histochemical, which will directly react with or bind to chemical groups of the target. Some histochemicals are typically co-incubated with a mordant or metal to allow staining. A cell containing sample may be incubated with a mixture of at least one histochemical that stains a component of interest and another histochemical that acts as a counterstain and binds a region outside the component of interest. Alternatively, mixtures of multiple probes may be used in the staining, and provide a way to identify the positions of specific probes. Procedures for staining cell containing samples are well known in the art.

An "image analysis system" as used herein is a system, e.g. a computer system, adapted to evaluate and process digital images, in particular images of tissue samples, in order to assist a user in evaluating or interpreting an image and/or in order to extract biomedical information that is implicitly or explicitly contained in the image. For example, the computer system can be a standard desktop computer system or a distributed computer system, e.g. a cloud system. Generally, computerized histopathology image analysis takes as its input a single- or multi-channel image captured by a camera and attempts to provide additional quantitative information to aid in the diagnosis or treatment.

Embodiments of the invention may be used for determining which sub-group of patients in a larger group of patients will likely profit from a particular drug. Personalized medicine (PM) is a new medical field whose aim is to provide effective, tailored therapeutic strategies based on the genomic, epigenomic and proteomic profile of an individual. PM does not only try to treat patient, but also to prevent patients from negative side effects of ineffective treatments. Some mutations that often occur when a tumor develops give rise to resistance to certain treatments. Hence, the mutational profile of a patient that may be revealed at least in part by tissue images of biomarker-specifically stained tissue samples will allow a trained MIL program to clearly decide if a particular treatment will be effective for an individual patient. Currently, it is necessary to determine in a trial and error approach if a prescribed medication is effective in a patient or not. The trial and error process may have many negative side effects such as undesired and complex drug interactions, frequent change of the drugs that are prescribed, long delays until an effective drug is identified, disease progression and others. PM is based on stratifying individuals into subpopulations that vary in their response to a therapeutic agent for their specific disease. For example, some ALK kinase inhibitors are useful drugs for treating about 5% of NSCLC lung cancer patients who have elevated expression in the ALK gene. However, after some time, the kinase inhibitors become ineffective due to mutations of the ALK gene or of other genes downstream of the signaling cascade of ALK. Therefore, intelligent molecular characterization of lung cancer patients allows for the optimal use of some mutation-specific drugs through stratification of patients. Hence, the "group of patients" from whom the training images or the test images are taken can be groups such as "100 breast cancer patients", 100 HER+ breast cancer patient", "200 colon cancer patients" or the like.

A "digital image" as used herein is a numeric representation, normally binary, of a two-dimensional image. Typically, tissue images are raster type images meaning that the image is a raster ("matrix") of pixels respectively having assigned at least one intensity value. Some multi-channel images may have pixels with one intensity value per color channel. The digital image contains a fixed number of rows and columns of pixels. Pixels are the smallest individual element in an image, holding antiquated values that represent the brightness of a given color at any specific point. Typically, the pixels are stored in computer memory as a raster image or raster map, a two-dimensional array of small integers. These values are often transmitted or stored in a compressed form. A digital image can be acquired e.g. by digital cameras, scanners, coordinate-measuring machines, microscopes, slide-scanning devices and others.

A "label" as used herein is a data value, e.g. a string or a numerical value, that represents and specifies a patient-related attribute value. Examples for a label can be "patient response to drug D=true", "patient response to drug D=false", "progression free survival time=6 month", and the like.

An "image tile" as used herein is a sub-region of a digital image. In general, the tiles created from a digital image can have any shape, e.g. circular, elliptic, polygonal, rectangle, square or the like and can be overlapping or non-overlapping. According to preferred embodiments, the tiles generated from an image are rectangular, preferably overlapping tiles. Using overlapping tiles may have the advantage that also tissue patterns that would otherwise be fragmented by the tile generation process are represented in a bag. For example, the overlap of two overlapping tiles can cover 20-30%, e.g. 25% of the area of a single tile.

According to embodiments, an image tile gallery, e.g. the image tile report gallery and/or the image similarity search tile gallery, is a grid style organization of tiles on a GUI, wherein the tiles are spatially organized in the image tile gallery independently of their spatial arrangement within the image from which the tiles were derived.

A "feature vector" as used herein is a data structure that contains information describing an object's important characteristics. The data structure can be a monodimensional or polydimensional data structure where particular types of data values are stored in respective positions within the data structure. For example, the data structure can be a vector, an array, a matrix or the like. The feature vector can be considered as an n-dimensional vector of numerical features that represent some object. In image analysis, features can take many forms. A simple feature representation of an image is the raw intensity value of each pixel. However, more complicated feature representations are also possible. For example, a feature extracted from an image or image tile can also be a SIFT descriptor feature (scale invariant feature transform). These features capture the prevalence of different line orientations. Other features may indicate the contrast, gradient orientation, color composition and other aspects of an image or image tile.

A "heat map" as used herein is a graphical representation of data where the individual values contained in a matrix are represented as colors and/or intensity values. According to some embodiments, the heat map is opaque and comprises at least some structures of the tissue slide image based on which the heat map is created. According to other embodiments, the heat map is semi-transparent and is displayed as an overlay on top of the tissue image used for creating the heat map. According to some embodiments, the heat map indicates each of a plurality of similarity scores or similarity score ranges via a respective color or pixel intensity.

A "biomarker specific stain" as used herein is a stain that selectively stains a particular biomarker, e.g. a particular protein like HER, but not other biomarkers or tissue components in general.

A "non-biomarker specific stain" as used herein is a stain that has a more generic binding behavior. A non-biomarker specific stain does not selectively stain an individual protein or DNA sequence, but rather stains to a larger group of substances and sub-cellular as well as supra-cellular structures having a particular physical or chemical property. For example, Hematoxylin and eosin respectively are non-biomarker-specific stains. Hematoxylin is a dark blue or violet stain that is basic/positive. It binds to basophilic substances (such as DNA and RNA, which are acidic and negatively charged). DNA/RNA in the nucleus, and RNA in ribosomes in the rough endoplasmic reticulum are both acidic because the phosphate backbones of nucleic acids are negatively charged. These backbones form salts with basic dyes containing positive charges. Therefore, dyes like hematoxylin bind to DNA and RNA and stain them violet. Eosin is a red or pink stain that is acidic and negative. It binds to acidophilic substances such as positively charged amino-acid side chains (e.g. lysine, arginine). Most proteins in the cytoplasm of some cells are basic because they are positively charged due to the arginine and lysine amino-acid residues. These form salts with acid dyes containing negative charges, like eosin. Therefore, eosin binds to these amino acids/proteins and stains them pink. This includes cytoplasmic filaments in muscle cells, intracellular membranes, and extracellular fibers.

An "attention machine learning logic program" as used herein is an MLL that has been trained to assign weights to particular parameters, whereby the weights indicate the importance and the attention other programs may spend on analyzing those parameters. The idea behind attention MLLs is to simulate the ability of the human brain to selectively focus on a subset of the available data that is of particular relevance in the current context. Attention MLLs are used e.g. in the text mining field for selectively assigning weights and computational resources to particular words which are of particular importance for deriving the meaning from a sentence. Not all words are equally important. Some of them characterize a sentence more than others. An attention model generated by training an attention MLL on a training data set may specify that a sentence vector can have more attention on "important" words. According to one embodiment, the trained attention MLL is adapted to compute weights for each feature value in each feature vector examined and for calculating the weighted sum of all feature values in each feature vector. This weighted sum embodies the whole feature vector of the tile.

According to embodiments, an attention MLL is a MLL comprising a neural attention mechanism that is adapted to equip a neural network with the ability to focus on a subset of its inputs (or features): it selects specific inputs. Let $x \in \mathbb{R}^d$ be an input vector, $z \in \mathbb{R}^k$ a feature vector, $a \in [0,1]^k$ an attention vector, $g \in \mathbb{R}^k$ an attention glimpse and $f_\phi(x)$ an attention network with parameters $\phi$.

Typically, attention is implemented as $$ag = f_\phi(x) = a \odot z,$$

where $\odot$ is element-wise multiplication, while $z$ is an output of another neural network $f_\theta(x)$ with parameters $\theta$. We can talk about soft attention, which multiplies features with a (soft) mask of values between zero and one, or hard attention, when those values are constrained to be exactly zero or one, namely $a \in \{0,1\}^k$. In the latter case, we can use the hard attention mask to directly index the feature vector: $g\sim = z[a]$ (in Matlab notation), which changes its dimensionality and now $g\sim \in \mathbb{R}^m$ with $m \le k$.

The term "intensity information" or "pixel intensity" as used herein is a measure of the amount of electromagnetic radiation ("light") captured on or represented by a pixel of a digital image. The term "intensity information" as used herein may comprise additional, related information, e.g. the intensity of a particular color channel. A MLL may use this information for computationally extracting derivative information such as gradients or textures contained in a digital image, and the derivative information may be implicitly or explicitly extracted from the digital image during training and/or during feature extraction by the trained MLL. For example, the expression "the pixel intensity values of a digital image correlate with the strength of one or more particular stains" can imply that the intensity information, including color information, allows the MLL and may also allow a user to identify regions in tissue sample having been stained with a particular one of said one or more stains. For example, pixels depicting a region of a sample stained with hematoxylin may have high pixel intensities in the blue channel, pixels depicting a region of a sample stained with fastRed may have high pixel intensities in the red channel.

A "fully convolutional neural network" as used herein is a neural network composed of convolutional layers without any fully-connected layers or multilayer perceptrons (MLPs) usually found at the end of the network. A fully convolutional net is learning filters in every layer. Even the decision-making layers at the end of the network learn filters. A fully convolutional net tries to learn representations and make decisions based on local spatial input.

According to embodiments, the fully convolutional network is a convolutional network with only layers of the form whose activation functions generate an output data vector $y_{ij}$ at a location (l, j) in a particular layer that satisfies the following properties:

$$y_{ij} = f_{ks}(\{x_{si+\delta i, sj+\delta j}\}_{0 \le \delta i, \delta j \le k})$$

Wherein $x_{ij}$ is a data vector at location (i; j) in a particular layer, and $y_{ij}$ is the data vector at said location in the following layer, wherein $y_{ij}$ is an output generated by the activation functions of the network, where k is called the kernel size, s is the stride or subsampling factor, and $f_{ks}$ determines the layer type: a matrix multiplication for convolution or average pooling, a spatial max for max pooling, or an elementwise nonlinearity for an activation function, and so on for other types of layers. This functional form is maintained under composition, with kernel size and stride obeying the transformation rule:

$$f_{ks} \circ g_{k's'} = (f \circ g)_{k'+(k-1)s', ss'}$$

While a general deep net computes a general nonlinear function, a net with only layers of this form computes a nonlinear filter, which is also referred to as a deep filter or fully convolutional network. An FCN naturally operates on an input of any size, and produces an output of corresponding (possibly resampled) spatial dimensions. For a more detailed description of the characteristics of several fully convolutional networks see Jonathan Long, Evan Shelhamer, and Trevor Darrell: *"Fully Convolutional Networks for Semantic Segmentation"*, CVPR 2015.

A "machine learning logic (MLL)" as used herein is a program logic, e.g. a piece of software like a trained neuronal network or a support vector machine or the like that has been or that can be trained in a training process and that—as a result of the learning phase—has learned to perform some predictive and/or data processing tasks based on the provided training data. Thus, an MLL can be a program code that is at least partially not explicitly specified by a programmer, but that is implicitly learned and modified in a data-driven learning process that builds one or more implicit or explicit models from sample inputs. Machine learning may employ supervised or unsupervised learning. Effective machine learning is often difficult because finding patterns is hard and often not enough training data are available.

The term "biomarker" as used herein is a molecule that may be measured in a biological sample as an indicator of tissue type, normal or pathogenic processes or a response to a therapeutic intervention. In a particular embodiment, the biomarker is selected from the group consisting of: a protein, a peptide, a nucleic acid, a lipid and a carbohydrate. More particularly, the biomarker may be a particular protein, e.g. EGRF, HER2, p53, CD3, CD8, Ki67 and the like. Certain markers are characteristic of particular cells, while other markers have been identified as being associated with a particular disease or condition.

In order to determine the stage of a particular tumor based on an image analysis of a tissue sample image, it may be necessary to stain the sample with a plurality of biomarker-specific stains. Biomarker-specific staining of tissue samples typically involves the use of primary antibodies which selectively bind to the biomarker of interest. In particular these primary antibodies, but also other components of a staining protocol, may be expensive and thus may preclude the use of available image analysis techniques for cost reasons in many application scenarios, in particular high-throughput screenings.

Commonly, tissue samples are stained with a background stain ("counter stain"), e.g. a hematoxylin stain or a combination of hematoxylin and eosin stain ("H&E" stain) in order to reveal the large-scale tissue morphology and the boundaries of cells and nuclei. In addition to the background stain, a plurality of biomarker-specific stains may be applied in dependence on the biomedical question to be answered, e.g. the classification and staging of a tumor, the detection of the amount and relative distribution of certain cell types in a tissue or the like.

BRIEF DESCRIPTION OF THE DRAWINGS

The patent or application file contains at least one drawing executed in color. Copies of this patent or patent application publication with color drawing(s) will be provided by the Office upon request and payment of the necessary fee. In the following embodiments of the invention are explained in greater detail, by way of example only, making reference to the drawings in which:

FIG. 13 shows a similarity search result based feature vectors extracted by a feature-extraction MLL trained on an proximity-based similarity labels.

FIG. 1 depicts a flowchart of a method according to an embodiment of the invention. The method can be used e.g. for the prediction of a patient-related attribute value of a patient such as, for example, a biomarker status, diagnosis, treatment outcome, microsatellite status (MSS) of a particular cancer such as colorectal cancer or breast cancer, micrometastases in Lymph nodes and Pathologic Complete Response (pCR) in diagnostic biopsies. The prediction is based on digital images of histology slides using deep-Learning based on—preferably hypothesis free—feature extraction.

Figure 1:
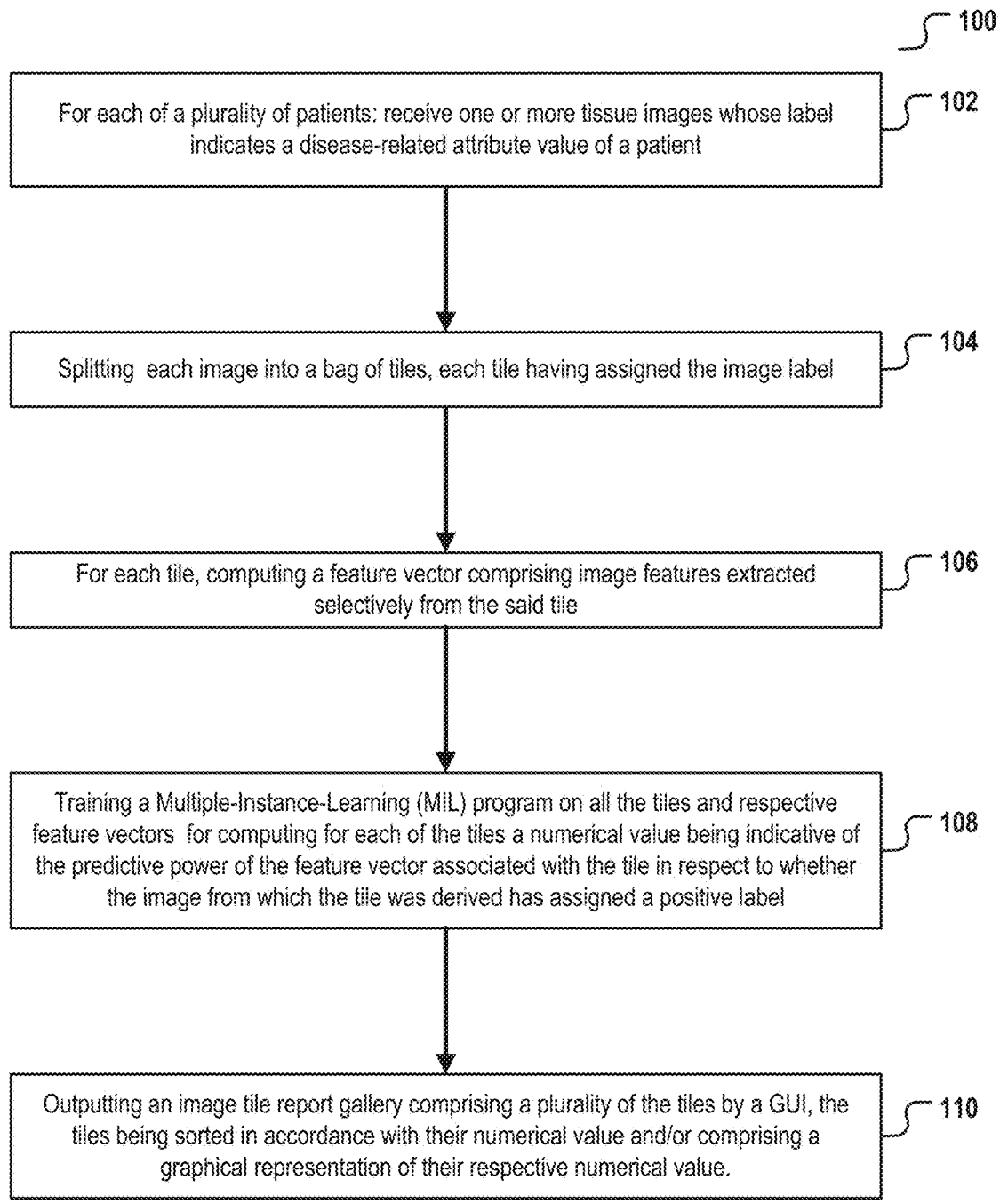
FIG. 1 depicts a flowchart of a method according to an embodiment of the invention.

The method 100 can be used for training a weakly supervised deep learning computer algorithm designed to identify and extract hitherto unknown predictive histological signatures. The method allows identifying tissue patterns being indicative of a patient-related attribute value.

Tissue specimen from patients may be provided e.g. in the form of FFPET tissue blocks. The tissue blocks need to be taken from patients with predetermined and pre-known endpoints (e.g. survival, response, gene signature, etc.) to be used as labels.

The tissue blocks are sliced and the slices set on microscopy slides. Then, the slices are stained with one or more histologically relevant stains, e.g. H&E and/or various biomarker specific stains. Images are taken from the stained tissue slices using e.g. a slide scanner microscope.

In a first step 102, an image analysis system (as described, for example, with reference to FIG. 2) receives for each patient in a group of patients at least one digital image 212 of a tissue sample of the said patient.

The reading can comprise reading the images from a database. For example, the images can be tissue sample images being many years old. Old image datasets may have the advantage that the outcome of many relevant events, e.g. treatment success, disease progression, side effects are meanwhile known and can be used for creating a training data set comprising tissue images having assigned the known events as labels. In addition, or alternatively, the images can be received directly from an image acquisition system, e.g. a microscope or a slide scanner. The labels can be assigned to the received images manually or automatically. For example, a user may configure the software of the slide scanner such that the acquired images are automatically labeled during their acquisition with a particular label. This may be helpful in a scenario where tissue sample images of large groups of patients having the same patient-related attribute value/endpoint are acquired sequentially, e.g. 100 tissue images of a first group of 100 breast cancer patients known to show a response to a particular drug D and 120 tissue images of a second group of 120 breast cancer patients known not to have shown this response. The user may have to set the label that is to be assigned to the captured images only once before the images of the first group are acquired and then a second time before the images of the second group are acquired.

For each patient, one or more images are retrieved. For example, the same tissue sample can be stained multiple times according to different staining protocols, whereby for each staining protocol an image is acquired. Alternatively, several adjacent tissue sample slices may respectively stained with the same or with different staining protocols and for each of the tissue sample slides an image is acquired. Each of the received images has assigned one out of at least two different predefined labels. Each label indicates a patient-related attribute value of the patient whose tissue is depicted in the labeled image. The attribute value can be of any type, e.g. Boolean, a number, a String, an ordinal parameter value etc.

Next in step 104, the image analysis system splits each received image into a set of image tiles 216. Thereby, each tile is assigned the label that was already assigned to the image used for creating the tile.

For example, the image data set published as a basis for the "CAMELYON16" challenge 2016 can be used as training data set. The CAMELYON16 data set consists of 270 whole slide images of H&E stained lymph node tissue sections of breast cancer patients is provided as a training image data set (160 images of normal tissue, 110 images with tumor metastases). The data set is available under https://camelyon16.grand-challenge.org/data/. At 10× magnification the images of this dataset can be used for generating 1,113,403 RGB tiles from non-background areas of size 256×256 pixels each with no overlap.

According to one embodiment, the received images as well as the generated tiles are multi-channel images. The number of tiles can be increased for enriching the training data set by creating modified copies of existing tiles having different sizes, magnification levels, and/or comprising some simulated artifacts and noise. In some cases, multiple bags can be created by sampling the instances in the bag repeatedly as described herein for embodiments of the invention and placing the selected instances in additional bags. This "sampling" may also have the positive effect of enriching the training data set.

In some cases, the feature vectors can be clustered into N clusters and M instances (tiles) can be randomly selected into pseudo-bags from each cluster to generate a cluster equivariant population of instances in the bags.

Next in step 106, the image analysis system computes, for each of the tiles, a feature vector 220. The feature vector comprises image features extracted selectively from a tissue pattern depicted in the said tile. Optionally, the feature vector can in addition comprise genetic features or other patient or patient-related data that is available for the patient from which the images and respective tiles have been derived. According to some embodiments, the feature extraction is performed by a trained feature extraction MLL. The feature extraction MLL can generate feature vectors for each tiles in the training data set while retaining the feature-vector-label relationship. However, other embodiments may use explicitly programmed feature extraction algorithms for providing a large variety of features which are descriptive of the tissue area depicted in the tile for which the feature vector is computed.

Next in step 108, a Multiple-Instance-Learning (MIL) program 226 is trained on all the tiles and respective feature vectors of all images received for all patients in the group. Thereby, the MIL program treats each set of tiles as a bag of tiles having the same label. The training comprises analyzing the feature vectors 220 of the tiles in the training data set for computing for each of the tiles a numerical value 228. This numerical value indicates the predictive power of the feature vector associated with the tile in respect to the label assigned to the image from which the tile was derived. In other words, this numerical value represents the predictive power, i.e., the "prognostic value/capability", of a particular feature vector for the occurrence/observation of the label assigned to the tile. As the features of the feature vectors have been extracted completely or at least partially from the image information contained in the respective tile, the feature vector represents optical properties of the tissue area depicted in this tile. Therefore, a feature vector can be regarded as an electronic tissue signature.

For example, the MIL program can be trained to predict the likely label or labels of a particular tissue region and/or can be trained to regress the labels if floating point label predictions are desired. In some cases, an additional attention-MLL is trained to learn which feature vectors are the most relevant for predicting the label. In some cases, the weights computed by the attention MLL is multiplied with each slide's feature vector values. As a result of the multiplication, a feature vector with weighted feature values is obtained for each tile and its feature vector and used as input to the MIL program at training time. In other embodiments the weights computed by the attention MLL are multiplied with the numerical value computed by the MIL for the feature vector of each tile. This creates a weighted numerical value used as indicator of the predictive power of a particular tile and its feature value in respect to the label. This weighted numerical value can be compared with the ground truth at train time to assess the accuracy of the trained MIL program. In some cases, average, min, max min-max pooling (or combination thereof) can be applied on the feature vectors obtained as tile-specific results by the MIL program during training in its permutation invariant transform operation.

Figure 3:
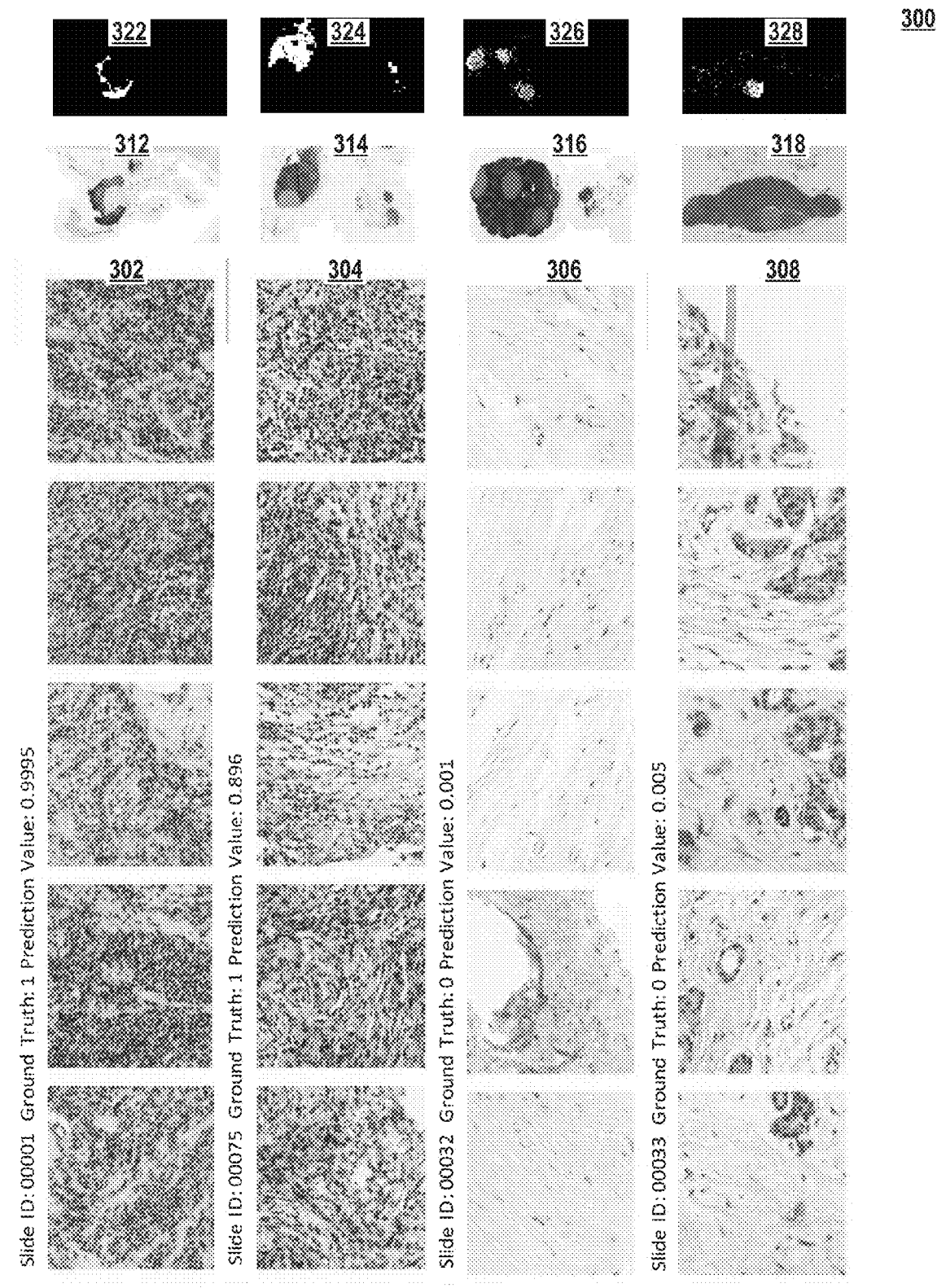
FIG. 3 depicts a GUI with a report image tile gallery according to an embodiment of the invention.

Next in step 110, the image analysis system outputs an image tile report gallery 206 via a GUI 232 generated by an image analysis software. An example of a GUI comprising a report image tile gallery is depicted in FIG. 3. The report gallery comprises a subset of the tiles, whereby the subset is sorted in accordance with their respectively computed numerical value. In addition, or alternatively, the report image tile gallery comprises a graphical representation of the numerical values associated with the respective tiles.

Finally, a trained MIL program is obtained as a result of the training phase. The trained MIL program can be applied on image tiles derived from other patient cohorts.

For testing purposes, it is also possible to split the available data set into a subset (comprising e.g. about 75% of the images) to be used as training data set and a further subset (comprising e.g. about 25% of the images) to be used as test data set. It was observed that the trained MIL program reached a high predictive value for relevant field of use (FOVs). These included tissue-patterns which have not until now been considered to have an impact on the prediction of pCR.

Hence embodiments of the invention may allow using the vast amount of data available in the drug development process, from histology and clinical imaging, from genomics and sequencing, from real world data and from diagnostic methods. The method may allow extracting novel insights and the development of new technologies.

In the context of pathology and histology analysis, the task of manually identifying the predictive underlying tissue texture or tissue related signature can be daunting due to the shear amount of information available in the multi-channel, multi stain multi-modality, high magnification images, each with billions of pixels. This exploration is therefore typically based on the exploration of human generated hypotheses and is thus limited to the borders of preexisting knowledge about the tumor and the biological mechanisms as well as by the complexity and labor requirements of manually reviewing a multitude of high magnification histology images. Embodiments of the invention may allow revealing hidden information in microscopic pathology histological tissue images such that both a machine learning logic and a human can interpret the features identified as having high predictive power.

According to embodiments, the trained MIL can be used for stratifying patient groups. This means the partitioning of patients by a factor other than the treatment given. Stratification can be performed based on patient-related attributes that are not used as the labels when training the MIL or the attention MLL. For example, such patient-related attributes can be age, gender, other demographic factors or a particular genetic or physiological trait. The GUI enables a user to select a sub-group of the patients whose tissue images were used for training the MIL based on any one of said patient-related attributes not used as label and compute the prediction accuracy of the trained MLL selectively on the sub-group. For example, the sub-group can consist of female patients or of patients older than 60 years. The accuracy obtained selectively for the respective subgroups, e.g. female/male or patients older than/younger than 60 may reveal a particular high or low accuracy of the trained MIL in some subgroups. This may allow confounding variables (variables other than those the researcher is studying), thereby making it easier for the researcher to detect and interpret relationships between variables and to identify patient groups who will benefit the most from a particular drug.

Figure 2:
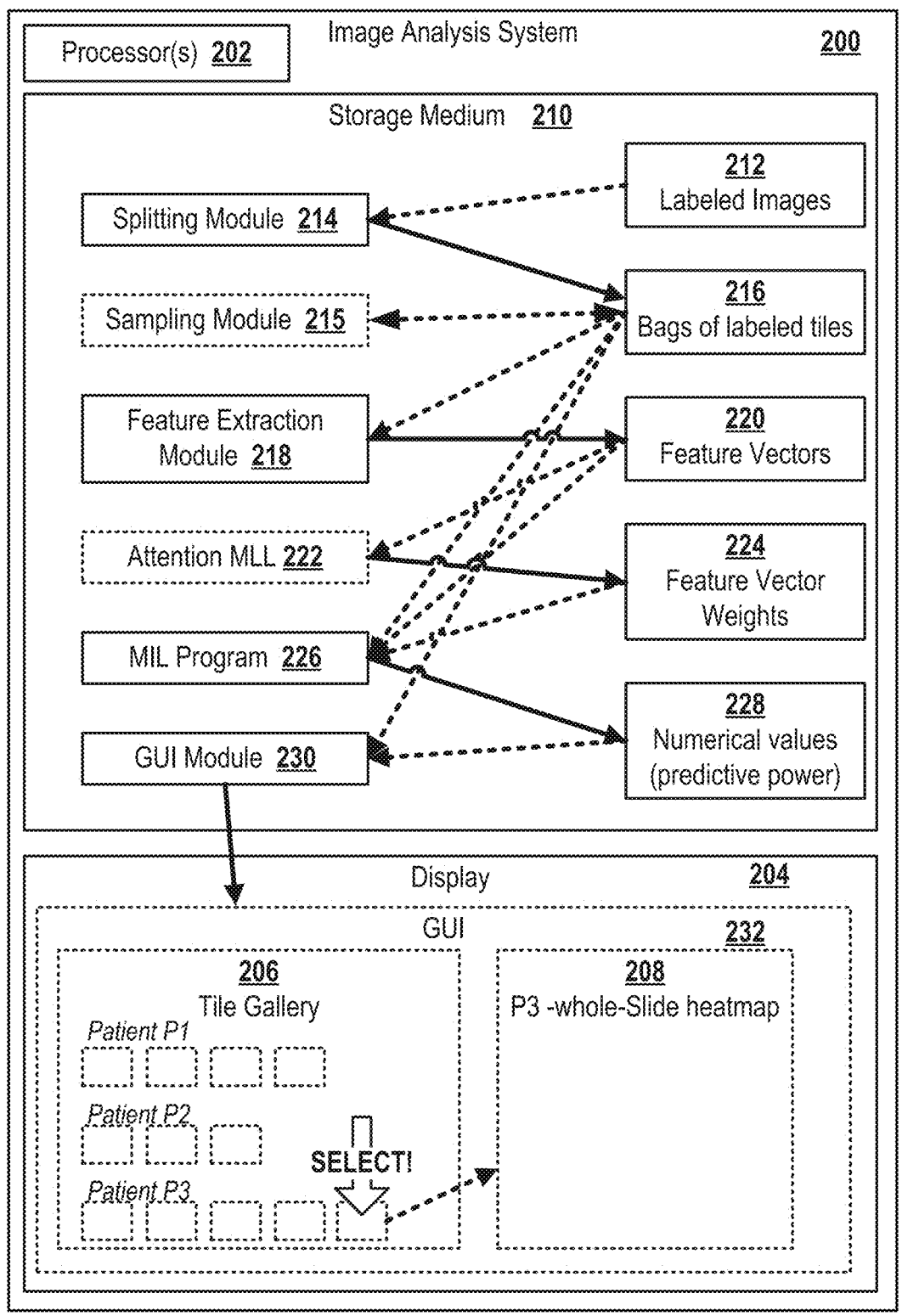
FIG. 2 depicts a block diagram of an image analysis system according to an embodiment of the invention.

FIG. 2 depicts a block diagram of an image analysis system 200 according to an embodiment of the invention.

The image analysis system 200 comprises one or more processors 202 and a volatile or non-volatile storage medium 210. For example, the storage medium can be a hard disk drive, e.g. an electromagnetic or flash drive. It can be a magnetic, semi-conductor based or optic data storage. The storage medium can be a volatile medium, e.g. the main memory, which only temporarily comprises data.

The storage medium comprises a plurality of labeled digital images 212 of tissue samples from patients with known endpoints.

The image analysis system comprises a splitting module 214 configured to split each of the images 212 into a plurality of tiles. The tiles are grouped into bags 216, whereby typically all tiles in the same bag are derived from the same patient. The label of the bag is the known endpoint of the patient and all tiles of the bag have assigned the bag's label.

A feature extraction module 218 is configured to extract a plurality of image features from each of the tiles 216. In some embodiments, the feature extraction module 218 can be a trained MLL or an encoding part of a trained MLL. the extracted features are stored as feature vectors 220 in association with the tiles from which they are derived in the storage medium 210. Optionally, the feature vectors can be enriched with features of the patient derived from other sources, e.g. genomic data, for example microarray data.

Optionally, the image analysis system can comprise a sampling module 215 adapted to select samples (subsets) of the images for training and test the trained MIL on the rest of the image tiles. The sampling module may perform a clustering of the tiles based on their feature vectors first before performing the sampling.

Optionally, the image analysis system can comprise an attention MLL program 222 that is configured to compute weights for each of the feature vectors and respective tiles. The weights may be used, together with the feature vectors, as input when training the MIL program 226 or for weighting the numerical values returned for each of the tiles by the MIL as a result of the training of the MIL program.

The image analysis system comprises a multiple instance learning program (MIL program 226). During the training, the MLL program 226 receives the feature vectors 220 (or the weighted feature vectors 224 generated by the attention MLL 222) as well as the labels assigned to the respective tiles. As a result of the training, a trained MIL program 226 is provided. In addition, for each of the tiles, a numerical value 228 is computed that is indicative of the predictive power of the tile and the tissue pattern depicted therein for the label assigned to the tile. These numerical values may also be referred to as "numerical tile relevance scores".

The image analysis system further comprises a module 230 configured to generate a GUI 232 that is displayed on a screen 204 of the image analysis system.

The GUI comprises a report tile gallery 206 comprising at least some of the tiles and the numerical values 228 computed for these tiles. The numerical values 228 can be displayed explicitly, e.g. as an overlay over the respective tile, and/or implicitly, e.g. in the form of a sort order of tiles being sorted in accordance with their respective numerical value 228. when a user selects one of the tiles, a whole slide heat map of the image from which the tile was originally derived is displayed. In other embodiments, the heat map may be displayed in addition to the report tile gallery 206 per default.

Each of the program modules 214, 215, 218, 222, 226, 230 can be implemented as sub-module of a large MIL training framework software application. alternatively, one or more of the modules may respectively represent stand-alone software application programs that are interoperable with the other programs and modules of the image analysis system. Each module and program can be, for example, a piece of software written in Java, Python, C#, or any other suitable programming language.

FIG. 3 depicts a GUI 300 with a report image tile gallery according to an embodiment of the invention. The report gallery (matrix of tiles below row labels 302, 304, 306 and 308) allows a user to explore tissue patterns identified by the MIL program to be of high predictive power in respect to a particular label. The gallery comprises the ones of the tiles having the highest numerical value in respect to a particular label of interest, e.g. "response to treatment with drug D=true" computed by the MIL. The tiles are grouped based on the tissue slide image they are derived from and are sorted within their group in accordance with their respective numerical value indicating the predictive power of the tile in respect to a particular label assigned to the images used for training the MIL. In addition, the gallery may comprise for each of the tiles in the gallery, the overall predictive accuracy that may have been automatically determined after the training. In addition, or alternatively, the report gallery can comprise the label assigned to the respective image and the predictive accuracy per bag obtained for this label. For example, the "ground truth=0" could represent the label "patient responded to drug D" and the "ground truth=1" could represent the label "patient did not respond to drug D". In case an attention MLL was used for computing weights, the sorting can also be based on a combined score value computed for each tile from a combination (e.g. a multiplication product) of the weight of the tile generated by the attention MLL and the numerical value computed by the MIL as described herein for embodiments of the invention. The highest numerical value of all tiles of a particular image computed by the MIL is displayed as the "predictive value" on top of the group of tiles derived from said image.

In the depicted gallery, tile row 302 shows six tiles of a first patient. The first one of said tile has assigned the highest numerical value (prognostic value) indicating the predictive power of a particular tissue slide/whole slide image in respect to a label. The first tile per slide-group may in addition or alternatively have assigned the highest combined value (derived from the numerical value provided by the MIL and from the weight computed by the attention MLL) of all tiles derived from a particular tissue slide image.

The highest numerical value can be displayed on top of the highest scoring tiles per patient as depicted in the GUI shown in FIG. 3.

The report tile gallery comprising only a subset of the tiles having the highest predictive power may be advantageous as a pathologist does not need to inspect the whole slide. Rather, the attention of the pathologist is automatically directed to a small number of sub-regions (tiles) of each whole-slide image whose tissue pattern has been identified to have the highest predictive power in respect to a label of interest.

According to the embodiment depicted in FIG. 3, the report image tile gallery shows image tiles derived from H&E stained images. The report image tile gallery is organized as follows:

Row 302 comprises the six tiles having assigned the highest numerical value (indicating the predictive power, i.e., the prognostic value) computed by the MIL program within all tiles derived from a particular whole slide image 312 of a first patient. According to other embodiments, the sorting is performed based on a score value that is identical to the numerical value computed by the MIL or that is a derivative value of the numerical value computed by the MIL. For example, the derivative value can be a combined score computed as a combination of the numeric value computed for a tile by the MIL and of a weight computed for said tile by an attention MLL. The combination can be, for example, a multiplication of the numerical value and the weight. According to still other embodiments, the tiles are sorted only in accordance with the weight computed by the attention-MLL and the numerical value computed by the MIL is displayed to the user in a different manner, e.g. in the form of numbers overlying the respective tile or number presented in spatial proximity to the respective tile.

The respective whole slide image 312 of the tissue sample of the first patient that was used for generating the tiles some of which being presented in row 312 is shown in spatial proximity to this selected set 312 of highly relevant tiles.

In addition, an optional relevance heat map 322 is shown that highlights all whole slide image regions whose numerical value computed by the MIL is similar to the numerical value of the one of the tiles of the image 312 for which the highest numerical value indicating the predictive power was computed. In this case, the one of the tiles for which the highest numerical value was computed is identified and selected automatically (e.g. the tile at the first position in row 312) and used as the basis for computing the relevance heat map 322. According to alternative implementation, the relevance heat map 322 represents not the similarity of a tile's numerical value to the highest numerical value computed for all the tiles of the image but rather represents the similarity of a tile to the highest combined score computed for all tiles of the image. The combined score can be a combination, e.g.

a multiplication, of a weight computed by an attention MLL for a tile and of the numerical value indicating the predictive power of the tile in respect to the label of the image that is computed by the MIL. According to still further embodiments, the relevance heat map 322 represents the similarity of a tile's weight computed by the attention MLL to the highest weight computed for all the tiles of the image by the attention MLL.

Column 304 comprises the six tiles having assigned the highest numerical value computed by the MIL program within all tiles derived from a particular whole slide image 314 of a second patient. The respective whole slide image 314 is shown in spatial proximity to this selected set of highly relevant tiles. In addition, a relevance heat map 324 is shown that highlights all whole slide image regions whose respective numerical values computed by the MIL are highly similar to the one of the tile of the whole slide image 314 for which the highest numerical value was computed by the MIL.

Column 306 comprises the six tiles having assigned the highest numerical value computed by the MIL program within all tiles derived from a particular whole slide image 316 of a third patient. The respective whole slide image 316 is shown in spatial proximity to this selected set of highly relevant tiles. In addition, a relevance heat map 326 is shown that highlights all whole slide image regions whose respective numerical values computed by the MIL are highly similar to the one of the tile of the whole slide image 316 for which the highest numerical value was computed by the MIL.

Column 308 comprises the six tiles having assigned the highest numerical value computed by the MIL program within all tiles derived from a particular whole slide image 318 of a patient. The respective whole slide image 318 is shown in spatial proximity to this selected set of highly relevant tiles. In addition, a relevance heat map 328 is shown that highlights all whole slide image regions whose respective numerical values computed by the MIL are highly similar to the one of the tile of the whole slide image 318 for which the highest numerical value was computed by the MIL.

According to embodiments, the relevance heat maps presented in the report tile gallery are indicative of the predictive power, or the attention-based weight, or of a combination thereof. In the depicted example, bright pixels in the heat maps depict areas in the image where tiles have a high predictive value, a high attention-based weight or combination thereof. According to embodiments, the computing of a relevance heat map comprises determining if the score of a tile (e.g. the numerical value, the weight or the combined value) is above a minimum percentage value of the score of the highest scoring tile of an image. If so, the respective tile in the relevance heat map is represented by a first color or a "bright" intensity value, e.g. "255". If not, the respective tile in the relevance heat map is represented by a second color or a "dark" intensity value, e.g. "0".

Figure 4:
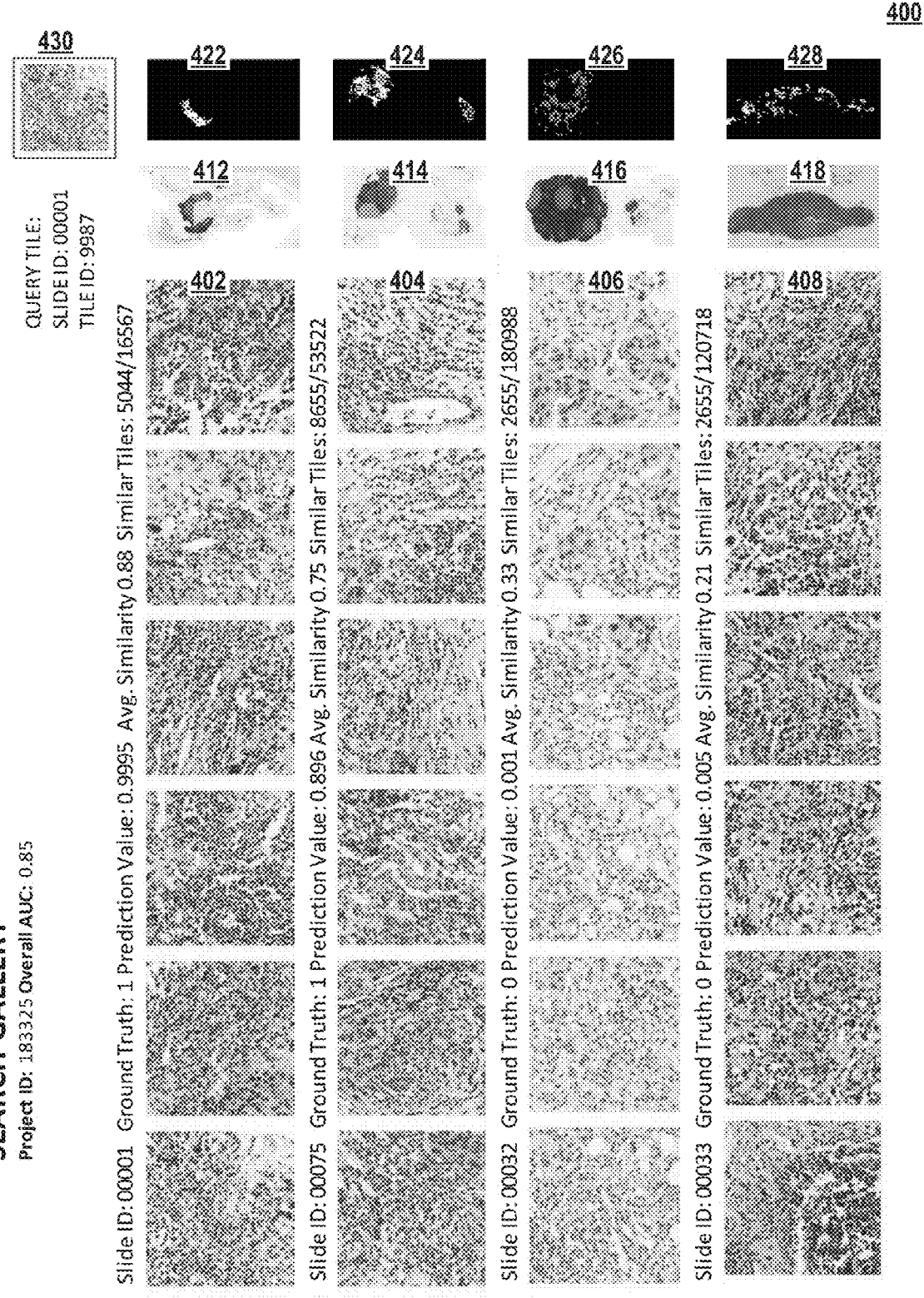
FIG. 4 depicts a GUI with a similarity search image tile gallery according to an embodiment of the invention.

Each tile in the report tile gallery can be selected by a user for initiating a similarity search (for example by double clicking on the tile or by selecting the tile with a single click and then selecting GUI element "Search") which will then display a similarity search tile gallery as shown, for example in FIG. 4.

The "blacklist" and "retrain" elements in the set of selectable GUI elements 310 enable a user to define a blacklist of tiles and to re-train the MIL program based on all tiles except the tiles in the blacklist and tiles highly similar to the tiles in the blacklist. For example, the blacklist can comprise set of manually selected tiles having a particularly low numerical value (prognostic value), e.g. because they comprise artifacts, or having a particularly high numerical value (the exclusion of tiles with very high predictive power may increase the capability of the MIL to identify additional, hitherto unknown tissue patterns also having predictive power in respect to the label of interest). The image analysis system can be configured to automatically identify, in response to a user adding a particular tile to the black list, all tiles whose feature vector based similarity to the feature vector of the tile added to the blacklist exceeds a minimum similarity threshold. The identified tiles are automatically added to the blacklist as well. When the user selects the Retrain-GUI element, the MIL is retrained on all tiles of the training data set except the tiles in the blacklist.

FIG. 4 depicts a GUI 400 with a similarity search image tile gallery according to an embodiment of the invention. The similarity search is triggered by a user-based selection of one 430 of the tiles in the report gallery.

The search identifies, within the tiles generated from each of the whole slide images 412-418, a sub-set of e.g. six most similar tiles based on a similarity of compared feature vectors. The tiles identified in the similarity search are grouped per-whole-slide image or per-patient and are sorted in descending order in accordance with their similarity to the tile 430 ("query tile") whose selection triggered the similarity search.

The whole slide images 412-418 and the similarity heat maps 422-428 indicate locations of tiles whose feature vectors (and hence, depicted tissue patterns) are the most similar to the feature vector of the selected tile.

Optionally, the similarity search tile gallery in addition comprises one or more the following data:
 the label assigned to the image the depicted tiles were derived from; one label depicted in FIG. 4 is "ground truth: 0";
 a predictive accuracy computed by the MIL program per bag (image) in respect to the bag's label;
 A count of similar tiles in a whole-slide image and/or the percentage (fraction) of the similar tiles in comparison to the non-similar ones (e.g. by thresholding)
 The average, median or histogram of similarity values of all tiles in a whole-slide-image.

Figure 5:
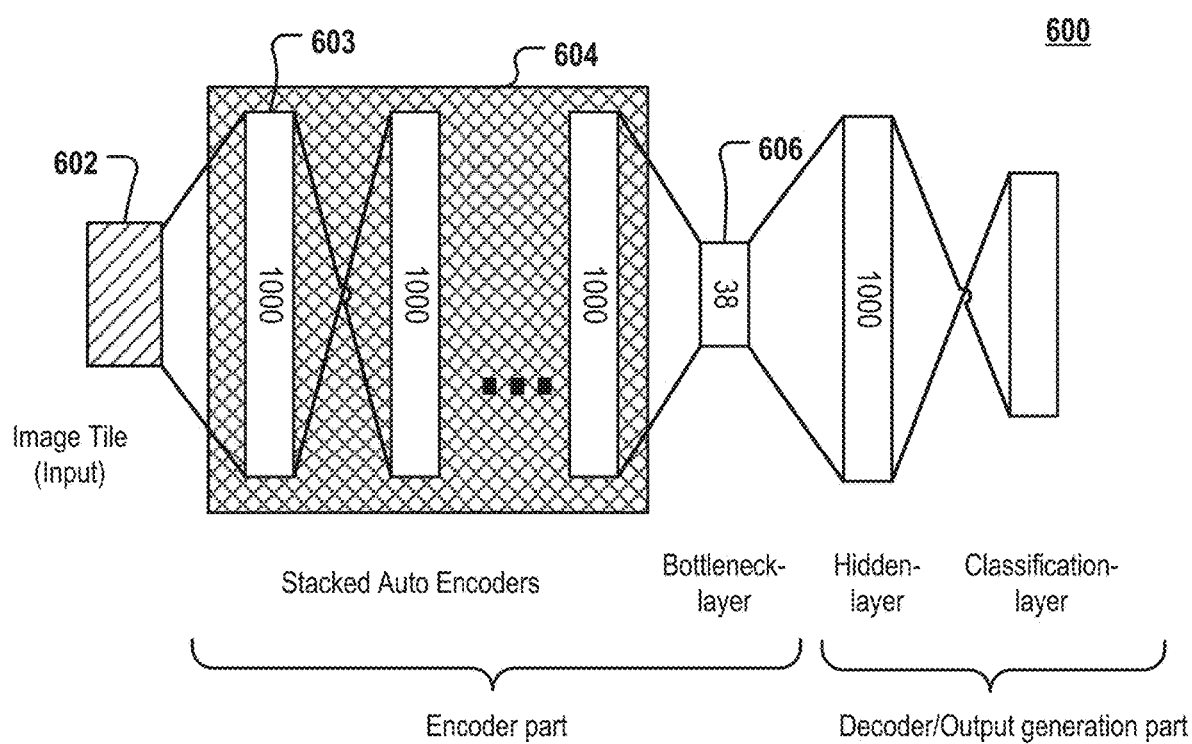
FIG. 5 depicts a network architecture of a feature extraction MLL program according to an embodiment of the invention.

FIG. 5 depicts a network architecture 600 of a feature extraction MLL program according to an embodiment of the invention that supports a supervised learning approach for feature vector generation. A deep neural network consisting of a series 604 of auto-encoders is trained on a plurality of features extracted from image tiles in a layer-wise manner. The trained network is able to perform a classification task later, e.g. to classify the tissue depicted in a tile into one of the classes "stroma tissue", "background slide region", "tumor cells", "metastatic tissue" based on optical features extracted from the image tiles. The network architecture comprises a bottleneck layer 606 that has significantly a less neurons than the input layer 603 and that may be followed by a further hidden layer and a classification layer. According to one example, the bottleneck layer comprises about 1.5% of the number of neurons of the input layer. Potentially there are many hundred or even many thousand hidden layers between the input layer and the bottleneck layer, and features extracted by the bottleneck layer may be referred to as "deep bottleneck features" (DBNF).

Figure 6:
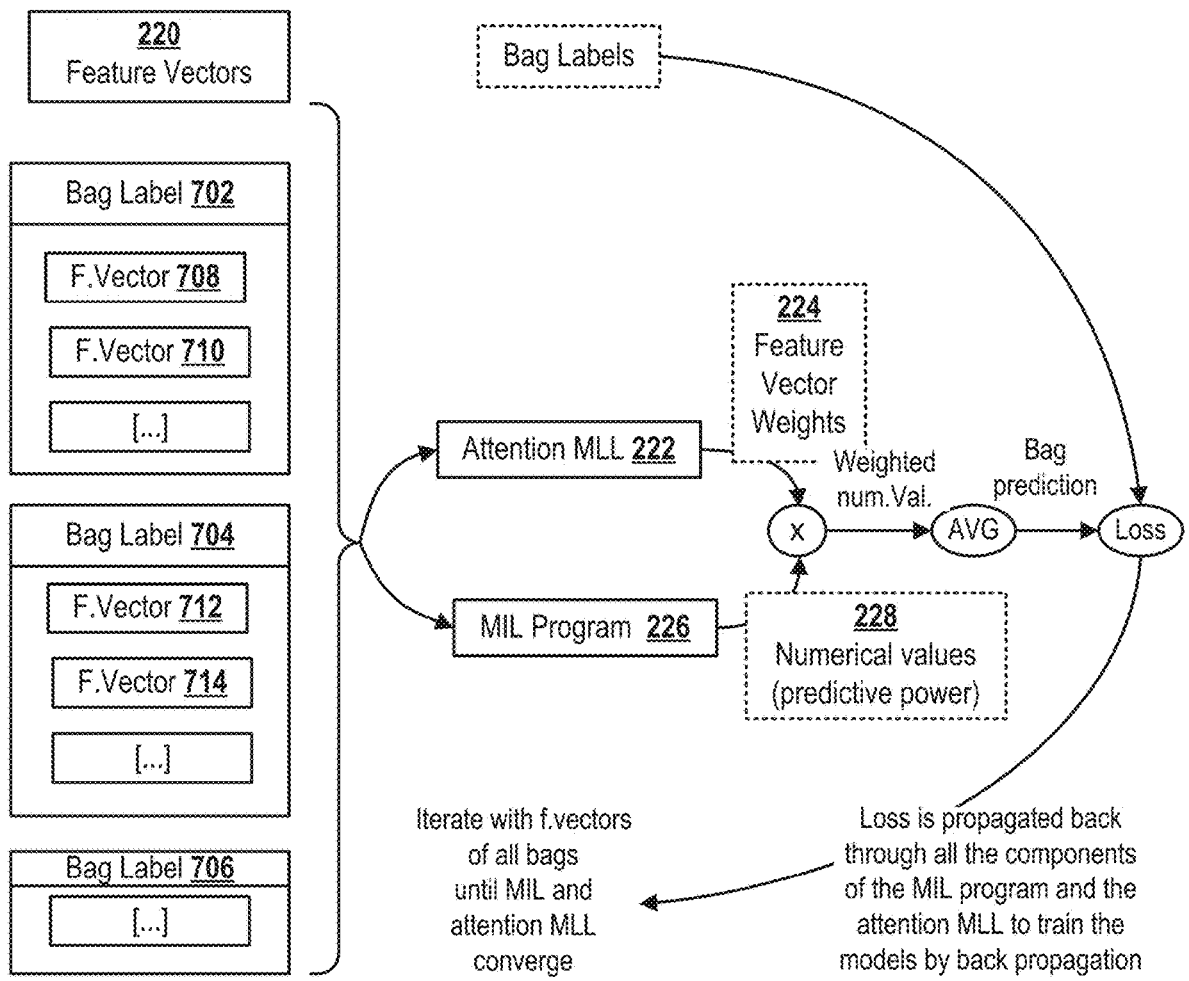
FIG. 6 depicts one possible system architecture for combining a MIL program and an attention MLL.

FIG. 6 depicts one possible system architecture for combining a MIL program and an attention MLL. According to the depicted embodiment, the training of the MIL program comprises training an attention machine learning logic program 222 on the feature vectors 220, 708-714 and the labels 216, 702-706 of all tiles of all received images to compute a weight for each of the tiles. The weight computed by the attention MLL is indicative the predictive power of the feature vectors and respective tiles in respect to the patient-related attribute value represented by the label of the tile. Then, the machine learning system depicted in FIG. 6 computes, for each of the tiles obtained from the received training images, a combined predictive value. The combined predictive value is a function of the numerical value computed by the MIL for the tile and of the weight computed by the attention MLL for the tile. The combined numerical value can be, for example, a multiplication product or an average of the numerical value of the MIL and of the weight of the attention MLL. The combined numerical value is indicative of the predictive power of feature vectors and respective tiles in respect to the patient-related attribute value represented by the label of the tile. Then, loss values are computed which are indicative of the difference of the combined predictive value obtained for a particular label and the actual labels assigned to the tiles. Then, the model of the MIL program is adapted iteratively using back propagation based on the computed loss values.

Figure 7:
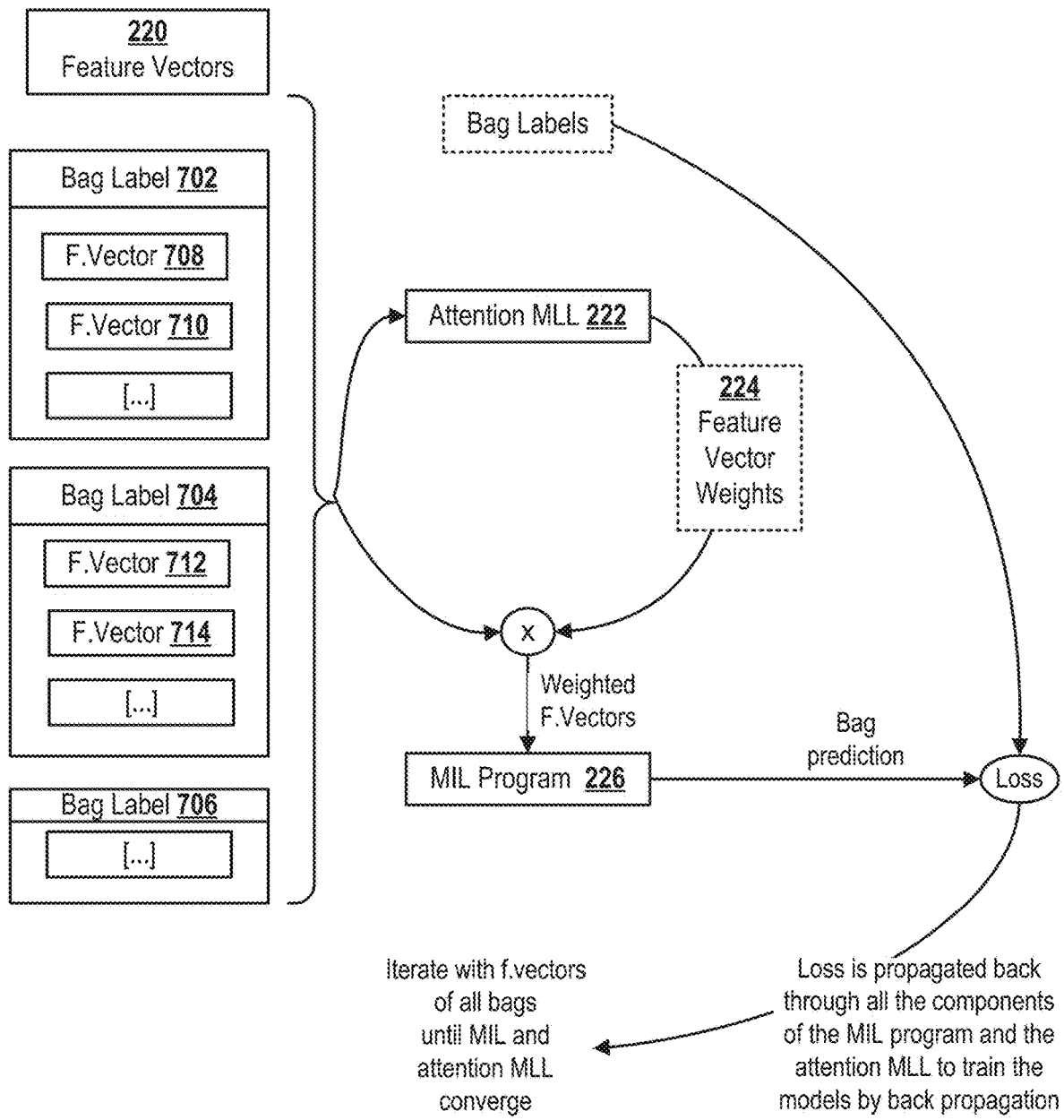
FIG. 7 depicts another possible system architecture for combining a MIL program and an attention MLL.

FIG. 7 depicts another possible system architecture for combining a MIL program and an attention MLL. The training of the MIL program comprises training an attention machine learning logic program 222—attention MLL program—on the feature vectors 220 and the labels 216 of all tiles of all received images to compute a weight for each of the tiles. The weight is indicative the predictive power of the feature vectors and respective tiles in respect to the patient-related attribute value represented by the label of the tile. Then, the machine learning system depicted in FIG. 7 computes, for each of the tiles, a weighted feature vector as a function of the weight computed by the attention MLL for the tile and of the feature vector extracted from the tile. The weighted feature vectors are input into the MIL for enabling the MIL to compute the numerical value for each of the tiles using the weighted feature vectors instead of the feature vectors originally extracted from the respective tiles and optionally also further data sources. Then, the MIL program computes loss values that are indicative of the difference of the numerical values obtained for a particular label and the actual labels assigned to the tiles. During the training, the MIL iteratively adapts its model using back propagation based on the computed loss values.

FIG. 8 illustrates spatial distances of tiles in a 2D and a 3D coordinate system that are used for automatically assigning similarity labels to pairs of tiles based on similarity labels automatically derived from the spatial proximity of tiles. Thereby, a training data set for training a feature-extraction MLL is provided that does not require manual annotation of images or tiles by a domain expert.

Figure 8A:
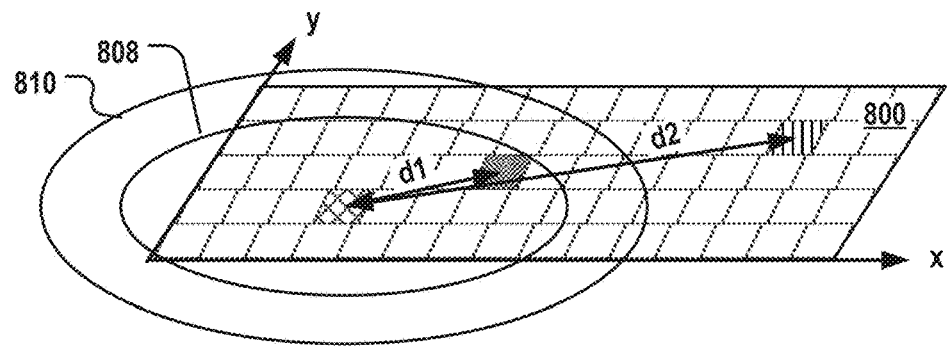
FIGS. 8A and 8B illustrate spatial distances of tiles in a 2D and a 3D coordinate system.
Figure 8A:
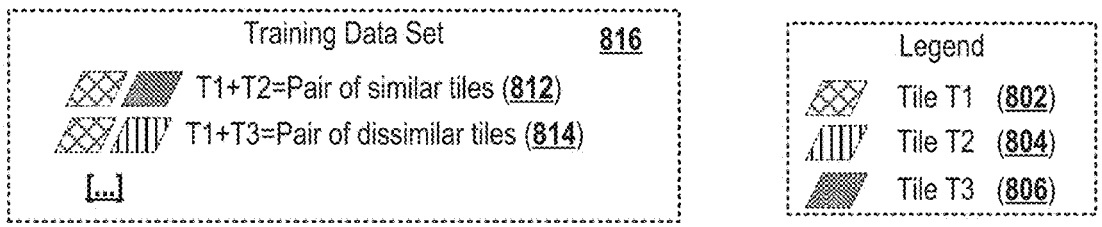

FIG. 8A illustrates spatial distances of tiles in a 2D coordinate system defined by the x and y axes of a digital tissue sample training image 800. The training image 800 depicts a tissue sample of a patient. After the tissue sample has been obtained from the patient, the sample was set on a microscopy slide and was stained with one or more histologically relevant stains, e.g. H&E and/or various biomarker specific stains. The training image 800 has been taken from the stained tissue sample using e.g. a slide scanner microscope. According to some implementation variants, at least some of the received training images are derived from different patients and/or derived from different tissue regions (biopsies) of the same patient and can therefore not be aligned to each other in a 3D coordinate system. In this case, the tile distance can be computed within a 2D space defined by the x and y coordinate of an image as described below.

The training image 800 is split into a plurality of tiles. For illustration purposes, the size of the tiles in FIG. 8A is larger than the typical tile size.

A training data set can be labelled automatically by the following approach: at first, a start tile 802 is selected. Then, a first circular area around this start tile is determined. The radius of the first circle is also referred to as first spatial proximity threshold 808. All tiles within this first circle, e.g. tile 806, are considered to be a "nearby" tile of the start tile 802. In addition, a second circular area around this start tile is determined. The radius of the second circle is also referred to as second spatial proximity threshold 810. All tiles outside of this second circle, e.g. tile 804, are "distant" tiles in respect to the start tile 802.

Then, a first set of tile pairs is created, wherein each tile pair of the first set comprises the start tile and a "nearby" tile of the start tile. For example this step can comprise creating as many tile pairs as nearby tiles are contained in the first circus. Alternatively, this step can comprise randomly selecting a subset of available nearby tiles and creating a tile pair for each of the selected nearby tiles by adding the start tile to the selected nearby tile.

A second set of tile pairs is created. Each tile pair of the second set comprises the start tile and a "distant" tile in respect to the start tile. For example, this step can comprise creating as many tile pairs as distant tiles are contained in the image 800 outside of the second circle. Alternatively, this step can comprise randomly selecting a subset of the available distant tiles and creating a tile pair for each of the selected distant tiles by adding the start tile to the selected distant tile.

Then, another tile within image 800 can be used as starting tile and the above mentioned steps can be performed analogously. This means that the first and second circles are redrawn using the new start tile as the center. Thereby, nearby tiles and distant tiles in respect to the new start tile are identified. The first set of tiles is supplemented with pairs of nearby tiles identified based on the new start tile and the second set of tiles is supplemented with pairs of distant tiles identified based on the new start tile.

Then, still another tile within image 800 can be selected as a start tile and the above mentioned steps can be repeated, thereby further supplementing the first and second tile pair sets with further tile pairs. The selection of new start tiles can be performed until all tiles in the image have once been selected as start tile or until a predefined number of tiles has been selected as start tile.

To each of the tile pairs in the first set, e.g. pair 812, the label "similar" is assigned. To each of the tile pairs in the second set, e.g. pair 814, the label "dissimilar" is assigned.

Figure 8B:
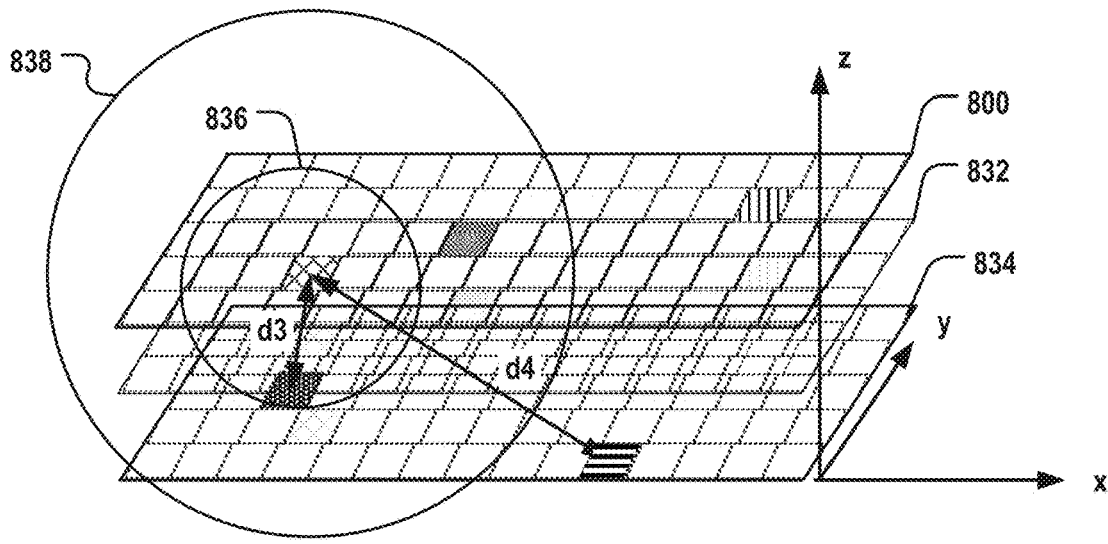
Figure 8B:
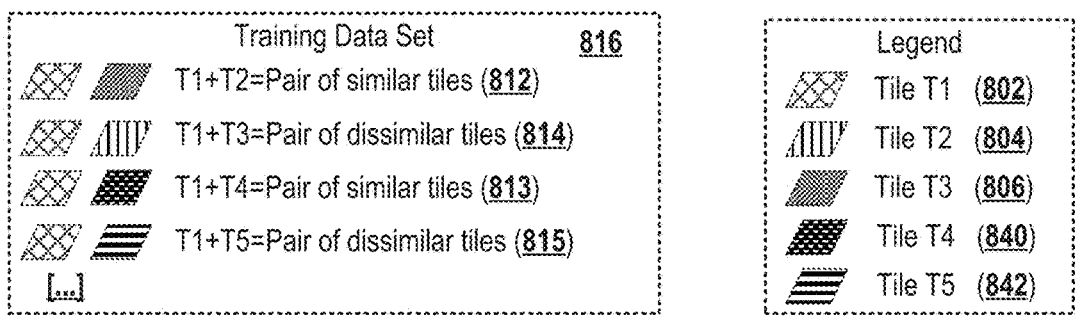

FIG. 8B illustrates spatial distances of tiles in a 3D coordinate system defined by the x and y axes of a digital tissue sample image 800 and a z axis corresponding to the height of a stack of images 800, 832, 834 aligned to each other in accordance with the relative position of a tissue block's tissue slices respectively depicted by the training images 800, 832, 834. The training images respectively depict a tissue sample derived from a single tissue block of a particular patient. The depicted tissue samples belong to a stack of multiple adjacent tissue slices. For example, this stack of tissue slices can be prepared ex-vivo from a FFPET tissue block. The tissue blocks are sliced and the slices set on microscopy slides. Then, the slices are stained as described for image 800 with reference to FIG. 8A.

As the tissue samples within this stack are derived from a single tissue block, it is possible to align the digital images 800, 832, 834 within a common 3D coordinate system, whereby the z-axis is orthogonal to the tissue slices. The z-axis is an axis orthogonal to the tissue slices. The distance of the images in z direction corresponds to the distance of the tissue slices depicted by the said images. The tile distance of a tile pair is computed within a 2D space in case the two tiles of a pair are derived from the same image. In addition, tile pairs can be created whose tiles are derived from different images aligned to each other in a common 3D coordinate system. In this case, the distance of the two tiles in a pair is computed using the 3D coordinate system.

Each of the aligned digital images is split into a plurality of tiles. For illustration purposes, the size of the tiles in FIG. 8B is larger than the typical tile size.

A training data set can be labelled automatically by the following approach: at first, a start tile 802 is selected. Then, tile pairs comprising the start tile and a nearby tile and tile pairs comprising the start tile and a distant tile are identified and labeled as described below.

A first 3D sphere around this start tile is determined. For illustration purposes, only a cross-section of the first sphere is shown. The radius of the first sphere is also referred to as first spatial proximity threshold 836. All tiles within this first sphere, e.g. tile 806 in image 800, but also tile 840 in image 834, are considered to be a "nearby" tile of the start tile 802. In addition, a second sphere around this start tile is determined. The radius of the second sphere is also referred to as second spatial proximity threshold 838. All tiles outside of this second sphere, e.g. tile 804 of image 800, but also tile 842 of image 834, are "distant" tiles in respect to the start tile 802.

A first set of tile pairs is created, wherein each tile pair of the first set comprises the start tile and a "nearby" tile of the start tile. For example this step can comprise creating as many tile pairs as nearby tiles are contained in the first sphere. Alternatively, this step can comprise randomly selecting a subset of available nearby tiles and creating a tile pair for each of the selected nearby tiles by adding the start tile to the selected nearby tile.

A second set of tile pairs is created. Each tile pair of the second set comprises the start tile and a "distant" tile in respect to the start tile. For example, this step can comprise creating as many tile pairs as distant tiles are contained in the images 800, 832, 834 outside of the second sphere. Alternatively, this step can comprise randomly selecting a subset of the available distant tiles and creating a tile pair for each of the selected distant tiles by adding the start tile to the selected distant tile.

Then, another tile within image 800 or within image 832, 834 can be used as starting tile and the above mentioned steps can be performed analogously. This means that the first and second spheres are redrawn using the new start tile as the center. Thereby, nearby tiles and distant tiles in respect to the new start tile are identified. The first set of tiles is supplemented with pairs of nearby tiles identified based on the new start tile and the second set of tiles is supplemented with pairs of distant tiles identified based on the new start tile.

The above mentioned steps can be repeated until every tile in each of the received images 800, 832, 834 has been selected as start tile (or until another termination criterium is fulfilled), thereby further supplementing the first and second tile pair sets with further tile pairs.

To each of the tile pairs in the first set, e.g. pair 812 and 813, the label "similar" is assigned. To each of the tile pairs in the second set, e.g. pair 814 and 815, the label "dissimilar" is assigned.

The circle and sphere-based distance computation illustrated in FIGS. 8A and 8B are only examples for computing distance-based similarity labels, in this case binary labels being either "similar" or dissimilar". Other approaches can likely be used, e.g. computing the Euclidian distance between two tiles in a 2D or 3D coordinate system and computing a numerical similarity value that negatively correlates with the Euclidean distance of the two tiles.

As the number of pixels that correspond to one mm tissue depends on various factors such as magnification of the image capturing device and the resolution of the digital image, all distance thresholds will herein be specified with respect to the depicted real physical object, i.e., a tissue sample or a slide covered by a tissue sample.

Figure 9:
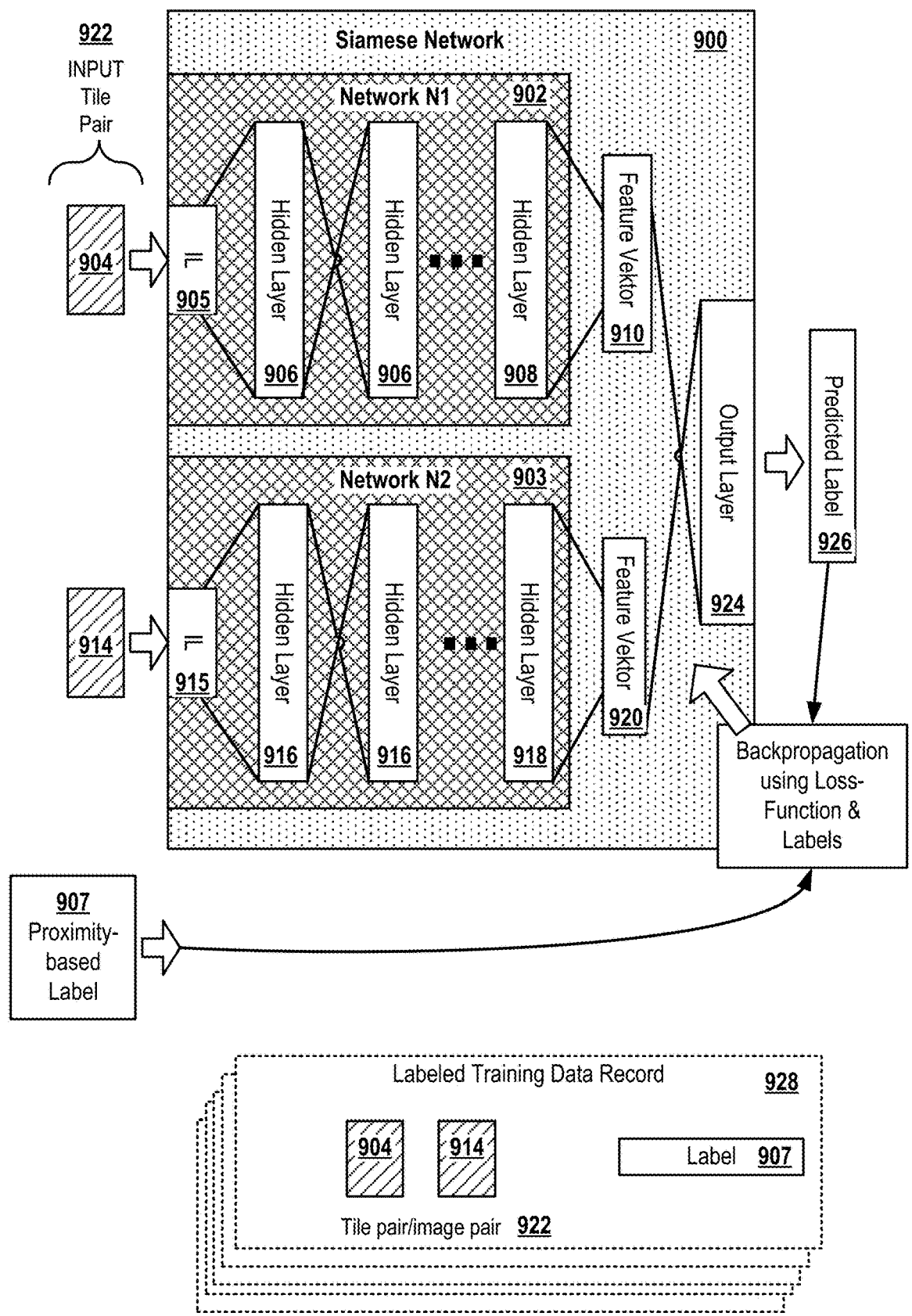
FIG. 9 depicts the architecture of a Siamese network according to an embodiment of the invention.

FIG. 9 depicts the architecture of a Siamese network that is trained according to an embodiment of the invention for providing a sub-network capable of extracting biomedically meaningful feature vectors from image tiles that are suited for performing a feature-vector based similarity search and/or a feature-vector based clustering of tiles. The Siamese network 900 is trained on an automatically labeled training data set according comprising tile pairs with proximity-based similarity labels that is automatically created as described, for example, with reference to FIGS. 8A and/or 8B.

The Siamese network 900 consists of two identical sub networks 902, 903 joined at their output layer 924. Each network comprises an input layer 905, 915 adapted to receive a single digital image (e.g. a tile) 954, 914 as input. Each sub-network comprises a plurality of hidden layers 906, 916, 908, 918. A one-dimensional feature vector 910, 920 is extracted from one of the two input images by a respective one of the two sub networks. Thereby, the last hidden layer 908, 918 of each network is adapted to compute the feature vector and provide the feature vector to the output layer 924. The processing of the input images is strictly separated. This means, that sub-network only processes the input image 954 and sub-network only processes the input image 914. The only point where the information conveyed in the two input images is combined is in the output layer when the output layer compares the two vectors for determining vector similarity and hence, the similarity of the tissue patterns depicted in the two input images.

According to embodiments, each sub-network 902, 903 is based on a modified resnet-50 architecture (He et al., Deep Residual Learning for Image Recognition, 2015, CVPR'15). According to embodiments, the resnet-50 pretrained sub-networks 902, 903 were pre-trained on ImageNet. The last layer (that normally outputs 1,000 features) is replaced with a fully connected layer 408, 418 of a size having the desired size of the feature vector, e.g. size 128. For example, the last layer 908, 918 of each sub-network can be configured to extract features from the second last layer, whereby the second last layer may provide a much greater number of features (e.g. 2048) than the last layer 908, 418. According to embodiments, an optimizer, e.g. the Adam optimizer with the default parameters in PyTorch (learning rate of 0.001 and betas of 0.9, 0.999), and a batch size of 256 was used during the training. For data augmentation, random horizontal and vertical flips and/or a random rotation up to 20 degrees, and/or a color jitter augmentation with a value of 0.075 for brightness, contrast saturation and/or hue can be applied on the tiles for increasing the training data set.

When the Siamese network is trained on pairs of automatically labeled images, it is the objective of the learning process that similar images should have outputs (feature vectors) that are similar to each other, and dissimilar images should have outputs that are dissimilar to each other. This can be achieved by minimizing a loss function, e.g. a function that measures the difference between the feature vectors extracted by the two sub-networks.

According to embodiments, the Siamese neuronal network is trained on the pairs of tiles using a loss function such that the similarity of the feature vectors extracted by the two sub-networks for the two tiles of the pair respectively correlates with the similarity of the tissue patterns depicted in the two tiles of the pair.

The Siamese network can be, for example, a Siamese network described in Bromley et al., "Signature Verification using a 'Siamese' Time Delay Neural Network, 1994, NIPS'1994. Each sub-network of the Siamese network is adapted to extract a multi-dimensional feature vector from a respective one of two image tiles provided as input. The network is trained on a plurality of tile pairs having been automatically annotated with proximity-based tissue-pattern-similarity labels with the objective that tile pairs depicting similar tissue patterns should have outputs (feature vectors) that are close (similar) to each other, and tile pairs depicting dissimilar tissue patterns should have outputs that are far from each other. According to one embodiment, this is achieved by performing a contrastive loss as described e.g. in Hadsell et al., Dimensionality Reduction by Learning an Invariant Mapping, 2006, CVPR'06. The contrastive loss is minimized during the training. The contrastive loss CL can be computed, for example, according to $$CL=(1-y)2(f1-f2)+y*\max(0,m-L2(f1-f2)),$$

wherein f1,f2 are the outputs two identical sub networks, and y is the ground truth label for the tile pair: 0 if they are labeled "similar" (first set of tile pairs), 1 if they are labeled "dissimilar" (second set of tile pairs).

The training of the Siamese network 900 comprises feeding the network 900 with a plurality of automatically labeled similar 812, 813 and dissimilar 814, 815 tile pairs. Each input training data record 928 comprises the two tiles of the tile pair and its automatically assigned, spatial-proximity-based label 907. The proximity-based label 403 is provided as the "ground truth". The output layer 924 is adapted to compute a predicted similarity label for the two input images 904, 914 as a function of the similarity of the two compared feature vectors 908, 918. The training of the Siamese network comprises a back propagation process. Any deviation of the predicted label 926 from the input label 907 is considered to be an "error" or "loss" that is measured in the form of a loss function. The training of the Siamese network comprises minimizing the error computed by the loss function by iteratively using back propagation. The Siamese network 900 can be implemented, for example, as described by Bromley et al. in "Signature Verification using a "Siamese" Time Delay Neural Network", 1994, NIPS'1994.

Figure 10:
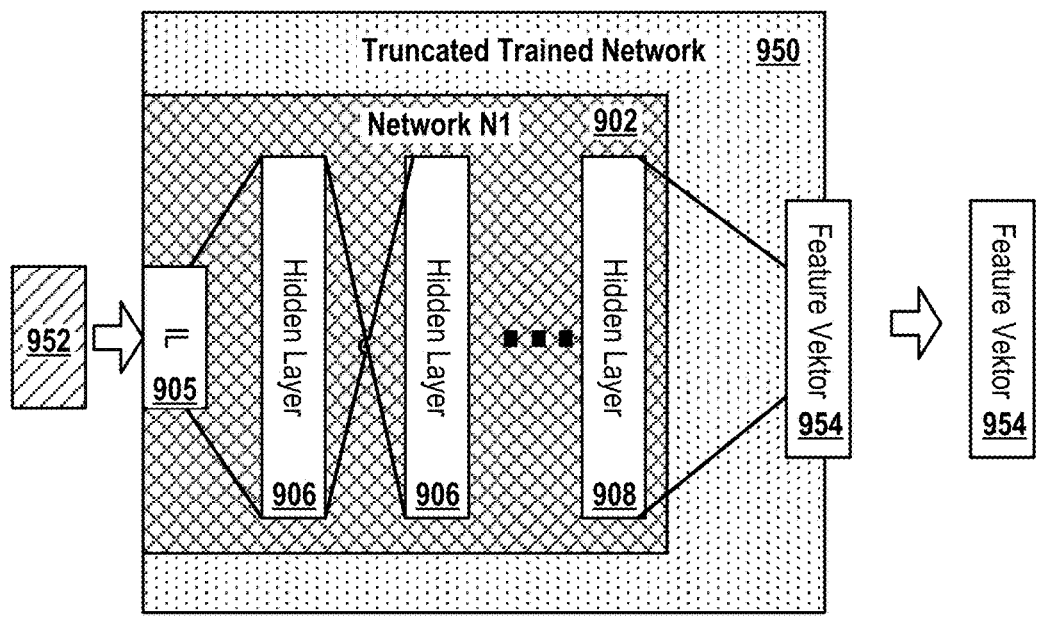
FIG. 10 depicts a feature-extraction MLL implemented as truncated Siamese network.

FIG. 10 depicts a feature-extraction MLL 950 implemented as truncated Siamese network as described, for example, with reference to FIG. 9.

The feature-extraction MLL 950 can be obtained, for example, by storing one of the sub-networks 902, 903 of a trained Siamese network 900 separately. In contrast to the trained Siamese network, the sub-network 90, 903 used as the feature-extraction-MLL requires only a single image 952 as input and does not output a similarity label but rather a feature vector 910 that selectively comprises values of a limited set of features having been identified during the training of the Siamese network 900 as being particularly characteristic for a particular tissue pattern and being particularly suited for determining the similarity of the tissue patterns depicted in two images by extracting and comparing this particular set of features from the two images.

Figure 11:
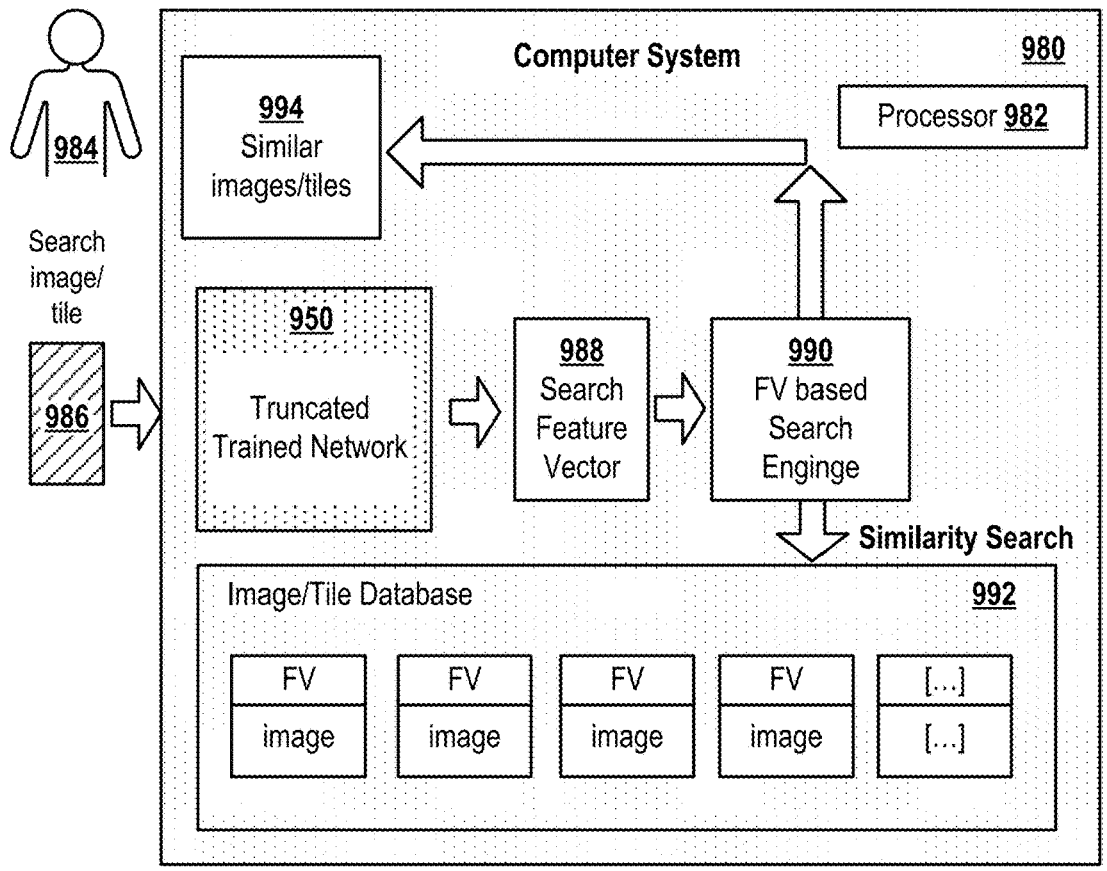
FIG. 11 depicts a computer system using a feature vector based similarity search in an image database.

FIG. 11 depicts a computer system 980 using a feature vector based similarity search in an image database. For example, the similarity search can be used for computing the search tile gallery an example of which is depicted in FIG. 4. The computer system 980 comprises one or more processors 982 and a trained feature-extraction MLL 950 that can be a sub-network of a trained Siamese network ("truncated Siamese network"). The system 980 is adapted to perform an image similarity search using the feature-extraction MLL for extracting a feature vector from the search image and from each of the searched images (tiles), respectively.

The computer system can be, for example, a standard computer system or a server that comprises or is operatively coupled to a database 992. For example, the database can be a relational BDSM comprising hundreds or even thousands of whole slide images depicting tissue samples of a plurality of patients. Preferably, the database comprises, for each of the images in the database, a respective feature vector that has been extracted by a feature output MLL 950 from the said image in the database. Preferably, the computation of the feature vector of each image in the database is performed in a single, pre-processing step before any such request is received. However, it is also possible to compute and extract the feature vectors for the images in the database dynamically in response to a search request. The search can be limited to the tiles of derived from a particular digital image, e.g. for identifying tiles within a single whole slide image that depict a tissue pattern that is similar to the tissue pattern depicted in the search image 986. The search image 986 can be, for example, a tile contained in the report tile gallery that was selected by the user.

The computer system comprises a user interface that enables a user 984 to select or provide a particular image or image tile that is to be used as search image 986. The trained feature-extraction MLL 950 is adapted to extract a feature vector 988 ("search feature vector") from the input image. a search engine 990 receives the search feature vector 988 from the feature output MLL 950 and performs a vector-based similarity search in the image database. The similarity search comprises comparing the search feature vector which each of the feature vectors of the images in the database in order to compute a similarity score as a function of the two compared feature vectors. The similarity score is indicative of the degree of similarity of the search feature vector with the feature vector of the image in the database and hence indicates the similarity of the tissue patterns depicted in the two compared images. The search engine 990 is adapted to return and output a search result 994 to the user. The search result can be, for example, one or more images of the database for which the highest similarity score was computed.

For example, if the search image 986 is an image tile known to depict breast cancer tissue, the system 980 can be used for identifying a plurality of other tiles (or whole slide images comprising such tiles) which depict a similar breast cancer tissue pattern.

Figure 12:
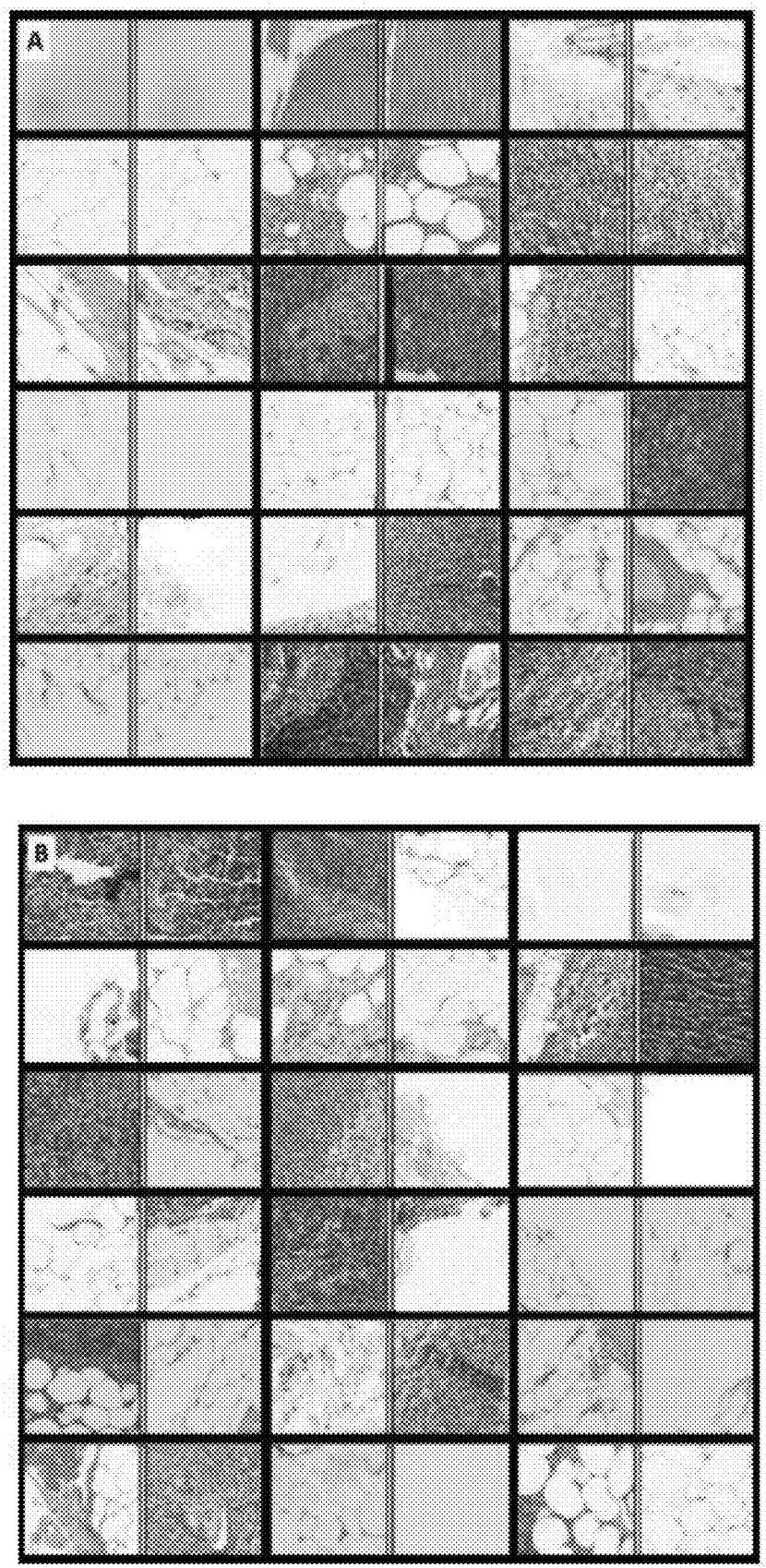
FIG. 12 shows "similar" and "dissimilar" tile pairs labeled based on their spatial proximity.

FIG. 12 shows two tile matrices, each matrix consisting of three columns, each column comprising six tile pairs. The first (upper) matrix shows a first set of tile pairs (A)

consisting of tiles that lie close to each other and that are automatically assigned the label "similar" tile pair. The second (lower) matrix shows a second set of tile pairs (B) lying far from each other and that are automatically assigned the label "dissimilar" tile pair. In some cases "similar" labeled tiles look dissimilar and "not similar" labeled tiles look similar. This noise is caused by the fact that at the border where two different tissue patterns meet, two nearby tiles may depict different tissue patterns and by the fact that even distant tissue regions may depict the same tissue pattern. This is an expected, inherent noise in the dataset generation process.

Applicant has observed that despite of this noise, the feature-extraction MLL trained on the automatically labeled data set is able to accurately identify and extract features that allow a clear distinction of similar and dissimilar tile pairs. Applicant assumes that that the observed robustness of the trained MLLs against this noise is based on the fact that region borders typically have less area than the region non-border areas.

According to embodiments, the quality of the automatically generated training data set is using, in a first step, a previously trained similarity network or an ImageNet pre-trained network to assess similarity of tile pairs, then a second step generate the similarity labels based on the spatial proximity of tiles as described herein for embodiments of the invention and then correct the pair labels where a strong deviation of the similarity of the two tiles determined in the first step on the one hand and in the second step in on the other hand is observed.

Figure 13:
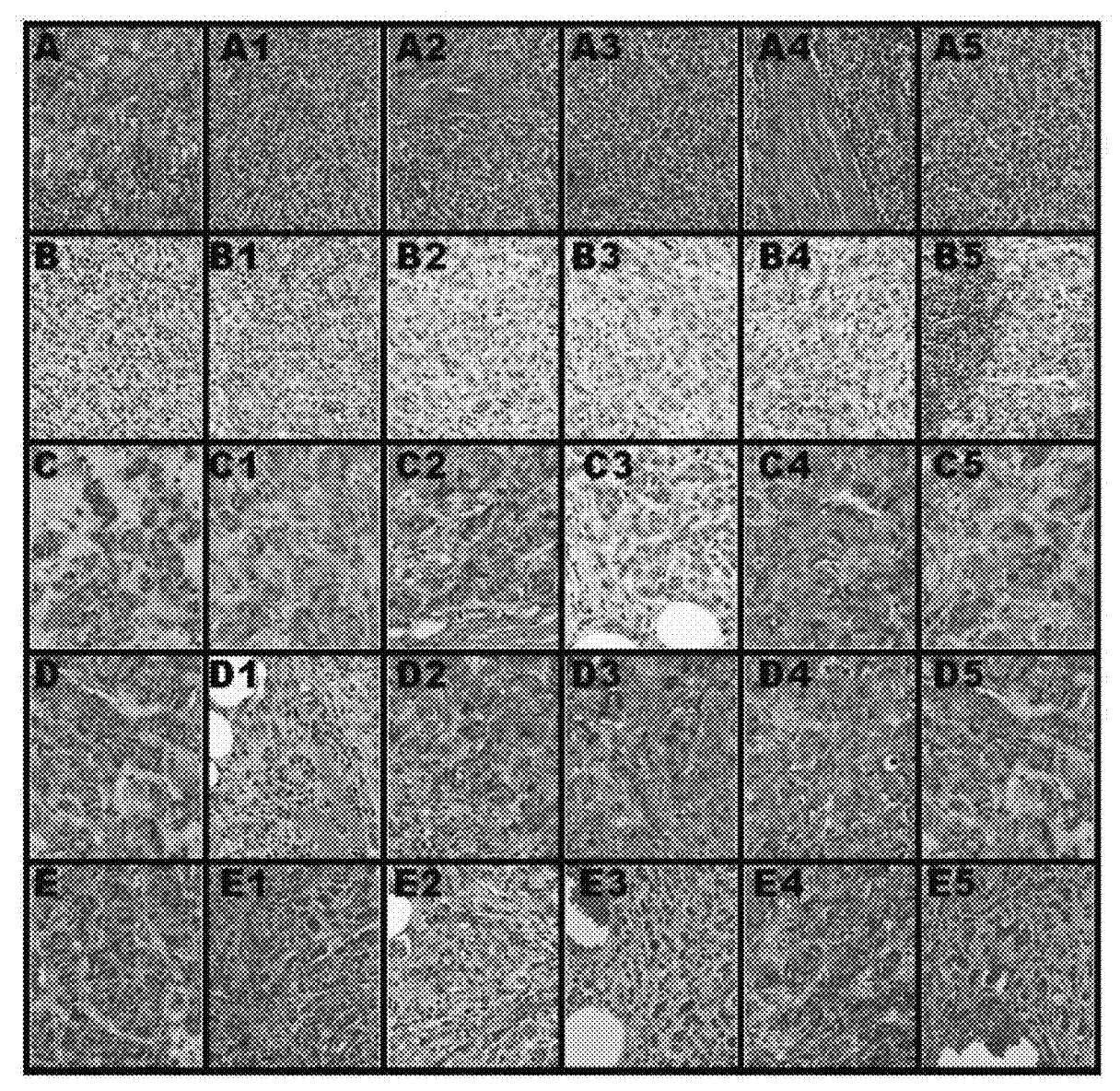

FIG. 13 shows a similarity search result based feature vectors extracted by a feature-extraction MLL trained on an proximity-based similarity labels. The 5 tumor query tiles are referred to as A, B, C, D, and E. The query tiles were used in the image retrieval task for respectively identifying and retrieving the 5 tiles other than the query slide (A1-A5, B1-B5, C1-C5, D1-D5, E1-E5), ranked by distance from low to high, using feature vectors extracted by a feature-extraction MLL trained on an automatically labeled data with proximity based labels. The target class (e.g. tumor) comprises only 3% of the tiles searched. Even though some retrieved tiles look very different than the query tile (e.g. C3 and C) all of the retrieved tiles except A4 have been verified by an expert pathologist to contain tumor cells (i.e. correct class retrieval).

| List of reference numerals | |
|---|---|
| 100 | method |
| 102-110 | steps |
| 200 | image analysis system |
| 202 | processor(s) |
| 204 | display |
| 206 | image tile gallery |
| 208 | whole slide heat m up ap |
| 210 | storage medium |
| 212 | digital images |
| 214 | splitting module |
| 216 | bags of labeled tiles |
| 218 | feature extraction module |
| 220 | feature vectors |
| 222 | attention machine learning logic program |
| 224 | feature vector weights |
| 226 | multiple instance learning program |
| 228 | numerical relevance scores of the tiles |
| 230 | GUI generation module |
| 232 | GUI |
| 300 | GUI comprising report tile gallery |
| 302 | first subset of similar tiles $1^{st}$ tissue pattern |
| 304 | 2.nd subset of similar tiles representing $2^{nd}$ tissue pattern |
| 306 | 3rd subset of similar tiles representing $3^{rd}$. tissue pattern |
| 308 | 4th subset of similar tiles representing $4^{th}$ tissue pattern |
| 310 | set of selectable GUI elements |
| 312 | whole slide image |
| 314 | whole slide image |
| 316 | whole slide image |
| 318 | whole slide image |
| 322 | relevance heat map |
| 324 | relevance heat map |
| 326 | relevance heat map |
| 328 | relevance heat map |
| 400 | GUI comprising similarity search tile gallery |
| 402 | first subset of similar tiles $1^{st}$ tissue pattern |
| 404 | 2.nd subset of similar tiles representing $2^{nd}$ tissue pattern |
| 406 | 3rd subset of similar tiles representing $3^{rd}$. tissue pattern |
| 408 | 4th subset of similar tiles representing $4^{th}$ tissue pattern |
| 410 | set of selectable GUI elements |
| 412 | whole slide image |
| 414 | whole slide image |
| 416 | whole slide image |
| 418 | whole slide image |
| 422 | similarity heat map |
| 424 | similarity heat map |
| 426 | similarity heat map |
| 428 | similarity heat map |
| 430 | query tile |
| 950 | network architecture of feature extraction MLL |
| 602 | image tile used as input |
| 603 | input layer |
| 604 | plurality of layers |
| 606 | bottleneck layer |
| 800 | digital tissue image sliced into a plurality of tiles |
| 802 | tile T1 |
| 804 | tile T2 |
| 806 | tile T3 |
| 808 | first spatial proximity threshold (2D) |
| 810 | second spatial proximity threshold (2D) |
| 812 | pair of tiles labeled "similar" |
| 813 | pair of tiles labeled "similar" |
| 814 | pair of tiles labeled "dissimilar" |
| 815 | pair of tiles labeled "dissimilar" |
| 816 | training data |
| 832 | digital tissue image aligned to image 300 |
| 834 | digital tissue image aligned to image 332 |
| 836 | first spatial proximity threshold (3D) |
| 838 | second spatial proximity threshold (3D) |
| 840 | tile T4 |
| 842 | tile T5 |
| 900 | Siamese network |
| 902 | sub-network |
| 903 | sub-network |
| 904 | first input tile |
| 905 | input layer of first network N1 |
| 906 | hidden layers |
| 907 | proximity-based ("measured") similarity label |
| 908 | hidden layer adapted to compute a feature vector for the first input tile |
| 910 | feature vector extracted from the first input tile 904 |
| 914 | second input tile |
| 915 | input layer of second network N2 |
| 916 | hidden layers |
| 918 | hidden layer adapted to compute a feature vector for the second input tile |
| 920 | feature vector extracted from the second input tile 914 |
| 922 | pair of input tiles |
| 924 | output layer joining networks N1, N2 |
| 926 | predicted similarity label |
| 928 | individual data record of training data set |
| 950 | feature-extraction MLL |
| 952 | individual input image/tile |
| 954 | feature vector |
| 980 | computer system |
| 982 | processor |
| 984 | user |
| 986 | individual input image/tile |
| 988 | search feature vector |

-continued

| | List of reference numerals |
|---|---|
| 990 | feature vector-based search engine |
| 992 | database comprising a plurality of images or tiles |
| 994 | returned similarity search results. |

The invention claimed is:

1. A method of identifying tissue patterns being indicative of a patient-related attribute value, the method comprising:
receiving, by an image analysis system, for each patient in a group of patients, at least one digital image of a tissue sample of the patient, the at least one image having assigned one out of at least two different predefined labels, each label indicating a patient-related attribute value of the patient whose tissue is depicted in the labeled image;
splitting, by the image analysis system, each received image into a set of image tiles, each tile having assigned the label assigned to the image used for creating the tile;
for each of the tiles, computing by the image analysis system, a feature vector comprising image features extracted selectively from a tissue pattern depicted in the said tile;
training a Multiple-Instance-Learning program on the tiles and respective feature vectors of the images received for all patients in the group, each set of tiles being treated by the MIL program as a bag of tiles having the same label, the training comprising analyzing the feature vectors for computing for each of the tiles a numerical value being indicative of the predictive power of the feature vector associated with the tile in respect to the label assigned to the image from which the tile was derived; and
outputting, via a GUI of the image analysis system, an image tile report gallery, the report gallery comprising a subset of the tiles, the subset of tiles being sorted in accordance with their respectively computed numerical value.

2. The method of claim 1, the received digital images comprising:
digital images of tissue samples whose pixel intensity values correlate with the amount of a non-biomarker specific stain, in particular hematoxylin stain or H&E stain; and/or
digital images of tissue samples whose pixel intensity values correlate with the amount of a biomarker specific stain, the biomarker-specific stain adapted to selectively stain a biomarker contained in the tissue sample;
a combination of
digital images of tissue samples whose pixel intensity values correlate with the amount of a first biomarker specific stain and of
digital images of tissue samples whose pixel intensity values correlate with the amount of a non-biomarker specific stain, the biomarker-specific stain adapted to selectively stain a biomarker contained in the tissue sample,
wherein all digital images depicting the same tissue sample and/or depicting adjacent tissue samples from the same patient have assigned the same label and wherein the MIL is configured to treat all tiles derived from the said digital images as members of the same bag of tiles.

3. The method of claim 1, the image tiles shown in the image tile report gallery being derived from one or more of the received images, the method comprising, for each of the one or more images in the report tile gallery:
Identifying the one of the tiles in the report gallery having been derived from the said image and having assigned the highest score of all the tiles derived from said image, the score being the numerical value computed for each tile by the MIL or being a weight computed for each tile by an attention-MLL or a combination of the said numerical value and the said weight computed by the MIL and the attention MLL for said tile;
For each of the other tiles of the image, computing a relevance indicator by comparing the score of the other tile with the score of the tile having the highest score, wherein the relevance indicator is a numerical value that negatively correlates with the difference of the score of the other tile with the score of the tile having the highest score;
Computing a relevance heat map for the image as a function of the relevance indicator, the pixel color and/or pixel intensities of the relevance heat map being indicative of the relevance indicator computed for the tiles in the said image; and
displaying the relevance heat map.

4. The method of claim 1, the image tiles shown in the report gallery being selectable, the GUI being configured for computing and displaying a similarity search tile gallery, the said computation comprising:
Receiving a user's selection of a particular one of the report gallery image tiles;
Identifying all tiles obtained from all the received images that depict a similar tissue pattern as the selected tile by identifying all tiles obtained from all the received images that have assigned a feature vector whose similarity to the feature vector of the selected tile exceeds a threshold value; and
Displaying the similarity search tile gallery, the similarity search tile gallery selectively comprising the said identified tiles;
Wherein the computation optionally further comprises determining the number and/or fraction of tiles within said identified tiles having assigned the same label as the selected tile; and wherein the displayed similarity search tile gallery further comprises the determined number and/or fraction.

5. The method of claim 1, wherein the image tiles in the report gallery are grouped based on the patients from whose tissue sample images the tiles were derived and/or wherein the image tiles in the report gallery are grouped based on the label assigned to the image from which the tiles were derived.

6. The method of claim 1, further comprising:
Computationally increasing the number of bags of tiles by creating additional sets of tiles, each additional set of tiles being treated by the MIL program as an additional bag of tiles having assigned the same label as the tissue image from which the source tiles were generated, wherein the creation of additional sets of tiles in particular comprises:
Applying one or more artifact generation algorithms on at least a subset of the tiles for creating new tiles comprising the artifact, and/or
Increasing or decreasing the resolution of at least a subset of the tiles for creating new tiles being more fine-grained or more coarse-grained than their respective source tiles.

7. The method of claim 1, further comprising:
compute clusters of tiles obtained from the one or more received digital images, wherein tiles are grouped into clusters based on the similarity of their feature vectors.

8. The method of claim 1, wherein the training of the MIL program comprises repeatedly sampling the sets of tiles for picking sub-sets of tiles from the sets of tiles, and training the MIL program on the sub-sets of tiles.

9. The method of claim 7, wherein the training of the MIL program comprises repeatedly sampling the sets of tiles for picking sub-sets of tiles from the sets of tiles, and training the MIL program on the sub-sets of tiles; and the sampling comprises selecting tiles from each of the tile clusters obtained for a patient such that the number of tiles in each sub-set of tiles created in the sampling corresponds to the size of the cluster from which the said tile is taken.

10. The method of claim 1, wherein the computing of the feature vector for each of the tiles comprises receiving patient-related data of the patient whose tissue sample is depicted in the tile and representing the patient-related data in the form of one or more features in the feature vector, the patient related data being in particular selected from a group comprising genomic data, RNA sequence data, known diseases of the patient, age, sex, metabolite concentrations in a body fluid, health parameters and current medication.

11. The method of claim 1, wherein the computing of the feature vectors is performed by a trained machine learning logic-, in particular by a trained fully convolutional neural network comprising at least one bottleneck-layer.

12. The method of claim 1, wherein the feature vectors are computed by a feature extraction machine learning logic having been trained on a training data set comprising labeled tile pairs, each label representing the similarity of two tissue patterns depicted by the tile pair and being computed as a function of the spatial distance of two tiles of the tile pair.

13. The method of claim 12, further comprising:
receiving a plurality of digital training images each depicting a tissue sample;
splitting each of the received training images into a plurality of tiles;
automatically generating tile pairs, each tile pair having assigned a label being indicative of the degree of similarity of two tissue patterns depicted in the two tiles of the pair, wherein the degree of similarity is computed as a function of the spatial proximity of the two tiles in the pair, wherein the distance positively correlates with dissimilarity;
training a machine learning logic—MLL—using the labeled tile pairs as training data to generate a trained MLL, the trained MLL having learned to extract a feature vector from a digital tissue image that represent the image in a way that images that are similar have similar feature vectors and images that are dissimilar have dissimilar feature vectors; and
using the said trained MLL or a component thereof for computing the feature vectors of the tiles.

14. The method of claim 13, wherein the trained MLL is a Siamese network comprising two neuronal sub-networks joined by their output layer, the method further comprising:
storing one of the sub-networks of the trained Siamese network separately on a storage medium; and
using the stored sub-network as the component of the trained MLL to be used for computing the feature vectors of the tiles.

15. The method of claim 1, wherein the label is selected from a group comprising:

An indication that the patient responded to a particular drug;
An indication that the patient has developed metastases or a particular form of metastases;
An indication that a cancer patient shows a pathological complete response (pCR) in response to a particular therapy;
An indication that the patient has a cancer with a particular morphological state or microsatellite status;
An indication that a patient has developed adverse reaction to a particular drug;
Genetic attributes, in particular gene signatures; and/or
RNA expression profiles.

16. The method of claim 1, the training of the MIL program comprising:
Training an attention machine learning logic program—attention MLL program—on the feature vectors and the labels of all tiles of all received images to compute a weight for each of the tiles, the weight being indicative the predictive power of the feature vectors and respective tiles in respect to the patient-related attribute value represented by the label of the tile;
Computing, for each of the tiles, a combined predictive value, the combined predictive value being a function of the numerical value computed by the MIL for the tile and of the weight computed by the attention MLL for the tile, the combined numerical value being indicative of the predictive power of feature vectors and respective tiles in respect to the patient-related attribute value represented by the label of the tile;
Computing loss values being indicative of the difference of the combined predictive value obtained for a particular label and the actual labels assigned to the tiles; and
adapting a model of the MIL program using back propagation based on the computed loss values.

17. The method of claim 1, the training of the MIL program comprising:
Training an attention machine learning logic program—attention MLL program—on the feature vectors and the labels of all tiles of all received images to compute a weight for each of the tiles, the weight being indicative the predictive power of the feature vectors and respective tiles in respect to the patient-related attribute value represented by the label of the tile;
Computing, for each of the tiles, a weighted feature vector as a function of the weight computed by the attention MLL for the tile and of the feature vector extracted from the tile;
Inputting the weighted feature vectors into the MIL for enabling the MIL to compute the numerical value for each of the tiles using the weighted feature vectors as the feature vectors;
Computing loss values being indicative of the difference of the numerical values obtained for a particular label and the actual labels assigned to the tiles; and
Adapting a model of the MIL program using back propagation based on the computed loss values.

18. The method of claim 1, further comprising:
receiving, by the image analysis system, for each patient in a further group of patients, at least one further digital image of a tissue sample of the patient, each further image having assigned one of the predefined labels;
splitting, by the image analysis system, each received further image into a set of further image tiles, each tile having assigned the label assigned to the image used for creating the further tile;

for each of the further tiles, computing, by the image analysis system, a further feature vector comprising image features extracted selectively from the said further tile and from a tissue pattern depicted therein;

applying the trained Multiple-Instance-Learning (MIL) program on the further tiles and respective further feature vectors of all further images received for all patients in the further group for computing for each of the further tiles a numerical value being indicative of the probability that the image from which the further tile was derived has assigned a particular label, the numerical value being computed as a learned non-linear transformation function of the feature vector of said further tile; and outputting, via the GUI of the image analysis system, a further image tile report gallery, the further report gallery comprising a plurality of the further tiles, the tiles being sorted in accordance with their respectively computed numerical value and/or comprising a graphical representation of their respective numerical value.

19. The method of claim 1, further comprising:

Automatically selecting or enabling a user to select one or more "high-predictive-power-tiles", wherein a high-predictive-power-tile is a tile whose numerical value indicating the predictive power of its feature vector in respect to a particular one of the labels exceeds a high-predictive-power-threshold; and/or Automatically selecting or enabling a user to select one or more "artifact-tiles", wherein an artifact-tile is a tile whose numerical value indicating the predictive power of its feature vector in respect to a particular one of the labels is below a minimum-predictive-power-threshold or depicts one or more artifacts;

In response to the selection of one or more high-predictive-power-tiles and/or artifact-tiles, automatically re-training the MIL program, thereby excluding the high-predictive-power-tiles and artifact-tiles from the training set.

20. An image analysis system for identifying tissue patterns being indicative of a patient-related attribute value, the image analysis system comprising:

at least one processor;

a volatile or non-volatile storage medium comprising digital tissue images of tissues of a group of patients, wherein for each patient in the group of patients, at least one digital image of a tissue sample of the patient is stored in the storage medium, the at least one image having assigned one out of at least two different pre-defined labels, each label indicating a patient-related attribute value of the patient whose tissue is depicted in the labeled image;

an image splitting module being executable by the at least one processor and being configured to split each of the images into a set of image tiles, each tile having assigned the label assigned to the image used for creating the tile;

a feature extraction module being executable by the at least one processor and being configured to compute, for each of the tiles, a feature vector comprising image features extracted selectively from a tissue pattern depicted in the said tile;

a Multiple-Instance-Learning program being executable by the at least one processor and being configured to receive, in a training phase of the MIL program, all the tiles and respective feature vectors of all images of all patients in the group, the MIL program being configured to treat each set of tiles as a bag of tiles having the same label during the training phase, the training comprising analyzing the feature vectors for computing for each of the tiles a numerical value being indicative of the predictive power of the feature vector associated with the tile in respect to the label assigned to the image from which the tile was derived; and a GUI generation module being executable by the at least one processor and being configured to generate and output a GUI comprising an image tile report gallery, the report gallery comprising a subset of the tiles, the subset of tiles being sorted in accordance with their respectively computed numerical value; and a display adapted for displaying the GUI with the image tile report gallery.

* * * * *